(12) United States Patent
Wheeler et al.

(10) Patent No.: US 12,365,893 B2
(45) Date of Patent: *Jul. 22, 2025

(54) SYSTEMS AND METHODS FOR NUCLEIC ACID PREPARATION

(71) Applicant: 10X Genomics, Inc., Pleasanton, CA (US)

(72) Inventors: Tobias Daniel Wheeler, Alameda, CA (US); Rajiv Bharadwaj, Pleasanton, CA (US); Katherine Pfeiffer, Berkeley, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 17/214,395

(22) Filed: Mar. 26, 2021

(65) Prior Publication Data
US 2022/0042009 A1 Feb. 10, 2022

Related U.S. Application Data

(63) Continuation of application No. 15/896,543, filed on Feb. 14, 2018, now Pat. No. 10,995,333, which is a
(Continued)

(51) Int. Cl.
*C12N 15/10* (2006.01)
*C12N 15/11* (2006.01)

(52) U.S. Cl.
CPC ..... *C12N 15/1096* (2013.01); *C12N 15/1065* (2013.01); *C12N 15/1093* (2013.01); *C12N 15/111* (2013.01); *C12N 2310/20* (2017.05)

(58) Field of Classification Search
CPC ............ C12N 15/1096; C12N 15/1065; C12N 15/1093; C12N 15/111; C12N 2310/20
See application file for complete search history.

(56) References Cited

U.S. PATENT DOCUMENTS

| 4,124,638 A | 11/1978 | Hansen |
| 5,185,099 A | 2/1993 | Delpuech et al. |

(Continued)

FOREIGN PATENT DOCUMENTS

| CN | 102766617 A | 11/2012 |
| CN | 105646719 A | 6/2016 |

(Continued)

OTHER PUBLICATIONS

NEB (New England Biolabs), DNase I product page, https://www.neb.com/en-us/products/m0303-dnase-i-rnase-free (Year: 2024).*
(Continued)

*Primary Examiner* — Aaron A Priest
*Assistant Examiner* — Matthew Harold Raymonda
(74) *Attorney, Agent, or Firm* — WILSON SONSINI GOODRICH & ROSATI

(57) ABSTRACT

The present disclosure provides methods and systems for nucleic acid processing. A method for preparing a sequencing set may include providing a template nucleic acid and amplifying the template nucleic acid to provide a complementary nucleic acid. Next, the complementary nucleic acid may be fragmented and barcoded to produce a first set of barcoded fragments comprising a plurality of first barcoded fragments. Next, the plurality of first barcoded fragments may be fragmented to yield a second set of barcoded fragments comprising a plurality of second barcoded fragments.

20 Claims, 9 Drawing Sheets

Related U.S. Application Data continuation of application No. PCT/US2018/016926, filed on Feb. 5, 2018.

(60) Provisional application No. 62/455,129, filed on Feb. 6, 2017.

(56) References Cited

U.S. PATENT DOCUMENTS

| | | |
|---|---|---|
| 5,231,972 A | 8/1993 | Galassi |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,806,058 B2 | 10/2004 | Jesperson et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,708,949 B2 | 5/2010 | Stone et al. |
| 7,741,463 B2 | 6/2010 | Gormley et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,003,312 B2 | 8/2011 | Krutzik et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,650,407 B2 | 5/2017 | Gartner et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,144,950 B2 | 12/2018 | Nolan |
| 10,151,003 B2 | 12/2018 | Fan et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,338,066 B2 | 7/2019 | Fan et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,697,008 B2 | 6/2020 | Blauwkamp et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |
| 11,952,626 B2 | 4/2024 | Pfeiffer et al. |
| 12,065,688 B2 | 8/2024 | Bell |
| 12,084,715 B1 | 9/2024 | Lund |
| 12,163,179 B2 | 12/2024 | Bell et al. |
| 12,169,198 B2 | 12/2024 | Price et al. |
| 12,188,014 B1 | 1/2025 | Price et al. |

(56) References Cited

U.S. PATENT DOCUMENTS

| | | |
|---|---|---|
| 12,235,262 B1 | 2/2025 | Giresi |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0027214 A1 | 2/2003 | Kamb |
| 2003/0036206 A1 | 2/2003 | Chien et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0124509 A1 | 7/2003 | Kenis et al. |
| 2003/0215862 A1 | 11/2003 | Parce et al. |
| 2004/0067493 A1 | 4/2004 | Matsuzaki et al. |
| 2004/0068019 A1 | 4/2004 | Higuchi et al. |
| 2005/0019839 A1 | 1/2005 | Jespersen et al. |
| 2005/0037397 A1 | 2/2005 | Mirkin et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0263457 A1 | 10/2011 | Krutzik et al. |
| 2011/0305761 A1 | 12/2011 | Shum et al. |
| 2012/0058468 A1 | 3/2012 | Mckeown |
| 2012/0071331 A1 | 3/2012 | Casbon et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0068797 A1* | 3/2014 | Doudna ............ H01L 21/02312 435/375 |
| 2014/0155295 A1 | 6/2014 | Hindson et al. |
| 2014/0221239 A1 | 8/2014 | Carman et al. |
| 2014/0228255 A1 | 8/2014 | Hindson et al. |
| 2014/0242664 A1 | 8/2014 | Zhang et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0357523 A1 | 12/2014 | Zeiner et al. |
| 2014/0378345 A1 | 12/2014 | Hindson et al. |
| 2015/0005188 A1 | 1/2015 | Levner et al. |
| 2015/0066385 A1 | 3/2015 | Schnall-Levin et al. |
| 2015/0220532 A1 | 8/2015 | Wong |
| 2015/0267191 A1 | 9/2015 | Steelman et al. |
| 2015/0292988 A1 | 10/2015 | Bharadwaj et al. |
| 2015/0361418 A1 | 12/2015 | Reed |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0017393 A1 | 1/2016 | Jacobson et al. |
| 2016/0017396 A1 | 1/2016 | Cann et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0201125 A1 | 7/2016 | Samuels et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0244828 A1 | 8/2016 | Mason |
| 2016/0257984 A1 | 9/2016 | Hardenbol et al. |
| 2016/0281160 A1 | 9/2016 | Jarosz et al. |
| 2016/0289669 A1 | 10/2016 | Fan et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0009274 A1 | 1/2017 | Abate et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080021 A1 | 3/2018 | Reuter et al. |
| 2018/0080075 A1 | 3/2018 | Brenner et al. |
| 2018/0105808 A1 | 4/2018 | Mikkelsen et al. |
| 2018/0195060 A1 | 7/2018 | Wang et al. |
| 2018/0208975 A1 | 7/2018 | Peterson et al. |
| 2018/0216162 A1 | 8/2018 | Belhocine et al. |
| 2018/0251825 A1 | 9/2018 | Stoeckius et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0320224 A1 | 11/2018 | Gaublomme et al. |
| 2018/0334670 A1 | 11/2018 | Bharadwaj et al. |
| 2018/0340169 A1 | 11/2018 | Belhocine et al. |
| 2018/0371545 A1 | 12/2018 | Wong et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0276818 A1 | 9/2019 | Gehring et al. |
| 2019/0300908 A1 | 10/2019 | Doudna et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |

(56) References Cited

U.S. PATENT DOCUMENTS

| | | |
|---|---|---|
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Alvarado Martinez |
| 2023/0167496 A1 | 6/2023 | Bava |
| 2024/0002914 A1 | 1/2024 | Pfeiffer et al. |
| 2024/0272044 A1 | 8/2024 | Bava |

FOREIGN PATENT DOCUMENTS

| | | |
|---|---|---|
| EP | 1019496 B1 | 9/2004 |
| EP | 1841879 A2 | 10/2007 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005040406 A1 | 5/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010132092 A2 | 11/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011154393 A1 | 12/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2014182835 A1 | 11/2014 |
| WO | WO-2014200767 A1 | 12/2014 |
| WO | WO-2015015199 A2 | 2/2015 |
| WO | WO-2015044428 A1 | 4/2015 |
| WO | WO-2015089406 A1 | 6/2015 |
| WO | WO-2015164212 A1 | 10/2015 |
| WO | WO-2016040476 A1 | 3/2016 |
| WO | WO-2016061517 A2 | 4/2016 |
| WO | WO-2016070037 A2 | 5/2016 |
| WO | WO-2016114970 A1 | 7/2016 |
| WO | WO-2016126871 A2 | 8/2016 |
| WO | WO-2016168584 A1 | 10/2016 |
| WO | WO-2016174229 A1 | 11/2016 |
| WO | WO-2017015075 A1 | 1/2017 |
| WO | WO-2017066231 A1 | 4/2017 |
| WO | WO-2017075265 A1 | 5/2017 |
| WO | WO-2017075294 A1 | 5/2017 |
| WO | WO-2017117358 A1 | 7/2017 |
| WO | WO-2017180949 A1 | 10/2017 |
| WO | WO-2017184707 A1 | 10/2017 |
| WO | WO-2017197343 A2 | 11/2017 |
| WO | WO-2018039338 A1 | 3/2018 |
| WO | WO-2018058073 A2 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018125982 A1 | 7/2018 |
| WO | WO-2018145041 A1 | 8/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019173638 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |

(56) References Cited

FOREIGN PATENT DOCUMENTS

| WO | WO-2021207610 A1 | 10/2021 |
|---|---|---|
| WO | WO-2021212042 A1 | 10/2021 |
| WO | WO-2021222301 A1 | 11/2021 |
| WO | WO-2021222302 A1 | 11/2021 |
| WO | WO-2022103712 A1 | 5/2022 |
| WO | WO-2022182785 A1 | 9/2022 |
| WO | WO-2022271908 A1 | 12/2022 |

OTHER PUBLICATIONS

Chen et al. Fusion Protein Linkers: Property Design and Functionality. Advanced Drug Delivery Reviews 65 (2013) 1357-1369 (Year: 2013).*
Schmidt, S.R. (2024). Fusion Proteins: Current Status and Future Perspectives. In: Gadamasetti, K., Kolodziej, S.A. (eds) Bioprocessing, Bioengineering and Process Chemistry in the Biopharmaceutical Industry. Springer, Cham. (Year: 2024).*
Abate, A.R. et al. "Beating Poisson encapsulation statistics using close-packed ordering" Lab on a Chip (Sep. 21, 2009) 9(18):2628-2631.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Ansorge. Next-generation DNA sequencing techniques. New Biotechnology, 25(4): 195-203 (2009).
Arslan, et al. Double-strand DNA end-binding and sliding of the toroidal CRISPR-associated protein Csn2. Nucleic acids research 41.12 (2013): 6347-6359.
Baret, "Surfactants in droplet-based microfluidics" Lab Chip (12(3):422-433 (2012).
Barrangou, R. and Luciano A. Marraffini (2014). CRISPR-Cas Systems: Prokaryotes Upgrade to Adaptive Immunity. Mod. Cell 54(2):234-244.
Beer et al. On-Chip, Real-Time, Single-Copy Polymerase Chain Reaction in Picoliter Droplets. Anal Chem 79:8471-8475 (2007).
Braeckmans et al., Scanning the Code. Modern Drug Discovery. 2003:28-32.
Brenda, 2.7.4.22: UMP kinase, printed from https://www.brenda-enzymes.org/all_enzymes.php?ecno=2.7.4.22 on Jun. 6, 2018, printed as pp. 1/4-4/4. (Year: 2018).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Burstein et al., (2017), "New CRISPR-Cas systems from uncultivated microbes." Nature. 542(7640):237-241.

Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chen et al. Fusion protein linkers: Property, design and functionality. Advanced Drug Delivery Reviews 65:1357-1369 (2013).
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Chu, WK. Microfluidic processors for accurate single-cell genome sequencing. UC San Diego Electronic Theses and Dissertations, https://scholarship.org/uc/itenn/6q11z7gnn, published Jan. 1, 2016. (Year: 2016).
Chylinski et al. The tracrRNA and Cas9 families of type II CRISPR-Cas immunity systems. RNA Biology 10(5):726-737 (2013).
Clausell-Tormos et al., "Droplet-based microfluidic platforms for the encapsulation and screening of mammalian cells and multicellular organisms", Chem. Biol. 15:427-437 (2008).
Cong et al. Multiplex genome engineering using CRISPR/Cas systems. Science 339(6121):819-23 (2013).
Co-pending PCT/US2019/046940, filed Aug. 16, 2019.
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/575,280, filed Sep. 18, 2019.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Datlinger et al. Pooled CRISPR screening with single-cell transcriptome readout. Nature Methods Advance Online Publication (Jan. 18, 2017). DOI: http://www.nature.com/doifinder/10.1038/nmeth.4177. 10 pages.
Delehanty, et al. Peptides for specific intracellular delivery and targeting of nanoparticles: implications for developing nanoparticle-mediated drug delivery. Ther Deliv. Sep. 2010;1(3):411-33.
Dey, et al. Integrated Genome and Transcriptome Sequencing from the Same Cell. Nature biotechnology 33.3 (2015): 285-289. PMC. Web. Dec. 18, 2017.
Ding, et al. Recent advances in genome editing using CRISPR/Cas9. Frontiers in plant science 7 (2016): 703.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
East-Seletsky, et al. Two distinct Rnase activities of CRISPR-C2c2 enable guide-RNA processing and RNA detection. Nature. 538. 7624 (Oct. 13, 2016): 270-273.
Esser-Kahn, et al. Triggered release from polymer capsules. Macromolecules. 2011; 44:5539-5553.
Fagerlund, et al. The CPf1 CRISPR-Cas protein expands genome-editing tools. Genome Biol. Nov. 17, 2015;16:251. doi: 10.1186/s13059-015-0824-9.
Friedland, et al. Heritable genome editing in C. elegans via a CRISPR-Cas9 system. Nat Methods. Aug. 2013; 10(8):741-3. doi: 10.1038/nmeth.2532. Epub Jun. 30, 2013.
Gaublomme, et al. Nuclei multiplexing with barcoded antibodies for single-nucleus genomics. Nat Commun. Jul. 2, 2019;10(1):2907. doi: 10.1038/s41467-019-10756-2.

(56) References Cited

OTHER PUBLICATIONS

Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl5):4742.
Jinek, et al. A programmable dual-RNA-guided DNA endonuclease in adaptive bacterial immunity. Science. Aug. 17, 2012;337(6096):816-21. doi: 10.1126/science.1225829. Epub Jun. 28, 2012.
Johansson, E. et al. "Structures of dCTP deaminase from *Escherichia coli* with bound substrate and product: reaction mechanism and determinants of mono- and biofunctionality for a family of enzymes" J. Biol. Chem. (2005) 280(4):3051-3059.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kester, et al. Single-Cell Transcriptomics Meets Lineage Tracing. Cell Stem Cell. Aug. 2, 2018;23(2):166-179. doi: 10.1016/j.stem.2018.04.014. Epub May 10, 2018.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).

Liu, et al. RNA and DNA targeting by a reconstituted Thermus thermophilus type III-A CRISPR-Cas system. Cell. vol. 168, pp. 121-134, Jan. 12, 2017.
Liu, et al. RNA and DNA targeting by a reconstituted Thermus thermophilus type III-A CRISPR-Cas system. PLoS One 12.1 (2017).
Love, "A microengraving method for rapid selection of single cells producing antigen-specific antibodies", Nature Biotech, 24:6 703 (Jun. 2006).
Macaulay, et al. G&T-seq: parallel sequencing of single-cell genomes and transcriptomes. Nature Methods, 2015, p. 1-7.
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015; 161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
Makarova et al. An updated evolutionary classification of CRISPR-Cas systems. Nat Rev Microbiol 13:722-736 (2015).
Makarova et al. Annotation and Classification of CRISPR-Cas Systems. Method Mol Biol 1311:47-75 (2015) .
Mali, P. "RNA-guided genome engineering via Cas9" Science (2013) 339(6121):823-826.
Margulies et al. "Genome sequencing in microfabricated high-density picoliter reactors", Nature (2005) 437:376-380.
Mazutis, et al. Single-Cell Analysis and Sorting Using Droplet-Based Microfluidics. Nat Protoc. 8(5): 870-891 (May 2013).
McCoy, R. et al. "Illumina TruSeq Synthetic Long-Reads Empower De Novo Assembly and Resolve Complex, Highly-Repetitive Transposable Elements" PLOS (2014) 9(9):e1016689.
McGinnis et al. MULTI-seq: sample multiplexing for single-cell RNA sequencing using lipid-tagged indices. Nat Methods. Jul. 2019;16(7):619-626. doi: 10.1038/s41592-019-0433-8. Epub Jun. 17, 2019.
McGinnis, et al. MULTI-seq: Scalable sample multiplexing for single-cell RNA sequencing using lipid-tagged indices. bioRxiv (2018) 387241; doi: https://doi.org/10.1101/387241.
Microfluidic ChipShop. Microfluidic product catalogue. Oct. 2009.
Mimitou, et al. Expanding the CITE-seq tool-kit: Detection of proteins, transcriptomes, clonotypes and CRISPR perturbations with multiplexing, in a single assay. bioRxiv preprint first posted online Nov. 8, 2018; doi: http://dx.doi.org/10.1101/466466.
Nakade et al. Cas9, Cpf1 and C2c1/2/3—What's next? Bioengineered, vol. 8, No. 3, pp. 265-273, Jan. 31, 2017. (Year: 2017).
Navin. The first five years of single-cell cancer genomics and beyond. Genome Res. Oct. 2015;25(10):1499-507. doi: 10.1101/gr.191098.115.
NEBNext® for Illumina®: NGS Sample Preparation. Version 3.0, New England BioLabs, Inc., printed as pp. 1-32, Dec. 2015. (Year: 2015).
Niewoehner, et al. Evolution of CRISPR RNA recognition and processing by Cas6 endonucleases. Nucleic acids research 42.2 (2013): 1341-1353.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.

(56) References Cited

OTHER PUBLICATIONS

Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Qi, et al. Repurposing CRISPR as an RNA-Guided Platform for Sequence-Specific Control of Gene Expression. Cell. Feb. 28, 2013;152(5):1173-83. doi: 10.1016/j.cell.2013.02.022.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rosenberg, et al. Single-cell profiling of the developing mouse brain and spinal cord with split-pool barcoding. Science. Apr. 13, 2018;360(6385):176-182. doi: 10.1126/science.aam8999. Epub Mar. 15, 2018.
Rotem, A. et al., "High-throughput single-cell labeling (Hi-SCL) for RNA-Seq using drop-based microfluidics" PLOS One (May 22, 2015) 0116328 (14 pages).
Rothberg, et al. An integrated semiconductor device enabling non-optical genome sequencing. Nature. 475 (2011): 348-352.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schmidt, et al. Quantitative analysis of synthetic cell lineage tracing using nuclease barcoding. ACS synthetic biology 6.6 (2017): 936-942.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors.Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Shendure, et al. Next-generation DNA sequencing. Nat Biotechnol. Oct. 2008;26(10):1135-45. doi: 10.1038/nbt1486.
Sinkunas, et al. Cas3 Nuclease-Helicase Activity Assays. CRISPR. Humana Press, New York, NY, 2015. 277-291.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Srivatsan, et al. Massively multiplex chemical transcriptomics at single-cell resolution. Science (New York, NY) 367.6473 (2020): 45-51.
Stoeckius, et al. Cell Hashing with barcoded antibodies enables multiplexing and doublet detection for single cell genomics. Genome Biol. Dec. 19, 2018;19(1):224. doi: 10.1186/s13059-018-1603-1.
Stoeckius, et al. Large-scale simultaneous measurement of epitopes and transcriptomes in single cells. bioRxiv 113068; doi: https://doi.org/10.1101/113068; (Mar. 2, 2017).
Stoeckius, et al. Simultaneous epitope and transcriptome measurement in single cells. Nature methods. Jul. 31, 2017.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tomita, et al. A novel enzyme, dCTP deaminase, found in Bacillus subtilis infected with phage PBS-I. Biochim Biophys Acta, Mar. 18, 1969 (Mar. 18, 1969), vol. 179, No. 1, pp. 18-27.
Tonelli, et al. Perfluoropolyether functional oligomers: unusual reactivity in organic chemistry. Journal of fluorine chemistry. 2002; 118(1)"107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Ullal et al. Cancer Cell Profiling by Barcoding Allows Multiplexed Protein Analysis in Fine- Needle Aspirates. Sci Transl Med. Jan. 15, 2014; 6(219): 219ra9.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Valouev et al. "A High-resolution, Nucleosome Position Map of C. Elegans Reveals a Lack of Universal Sequence-dictated Positioning" Genome Res. (2008) 18(7):105-1063.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Wiedenheft, et al. RNA-guided genetic silencing systems in bacteria and archaea. Nature. Feb. 15, 2012;482(7385):331-8. doi: 10.1038/nature10886.
Williams, et al. Amplification of complex gene libraries by emulsion PCR. Nature Methods. 2006;3(7):545-50.
Wong, et al. Multiplexed Barcoded CRISPR-Cas9 Screening Enabled By CombiGEM. PNAS. Mar. 1, 2016, vol. 113, pp. 2544-2549.
Zetsche et al. Cpf1 is a single RNA-guided endonuclease of a class 2 CRISPR-Cas system. Cell 163:759-771 (2015).
Zhang, et al. One-step fabrication of supramolecular microcapsules from microfluidic droplets. Science. Feb. 10, 2012;335(6069):690-4. doi: 10.1126/science.1215416.
Zhang, et al. The CRISPR associated protein Cas4 Is a 5' to 3' DNA exonuclease with an iron-sulfur cluster. PloS one 7.10 (2012).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
10X Genomics, Inc. CG000153 Rev A. Chromium Single Cell DNA Reagent Kits User Guide. 2018.

(56) References Cited

OTHER PUBLICATIONS

10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Bai, Y. et al. "Improving the oral efficacy of recombinant granulocyte colony-stimulating factor and transferrin fusion protein by spacer optimization," Pharm. Res. (2006) 23(9):216-21.
Co-pending U.S. Appl. No. 16/708,214, inventors Wheeler; Tobias Daniel et al., filed Dec. 9, 2019.
Co-pending U.S. Appl. No. 16/737,762, inventors Price; Andrew D et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Nemec; Corey M., filed Jan. 11, 2022.
Co-pending U.S. Appl. No. 17/580,947, inventor Gibbons; Michael, filed Jan. 21, 2022.
Co-pending U.S. Appl. No. 18/046,843, inventor Toh; Mckenzi, filed Oct. 14, 2022.
Co-pending U.S. Appl. No. 18/152,650, inventor Shastry; Shankar, filed Jan. 10, 2023.
Co-pending U.S. Appl. No. 18/392,684, inventors Fernandes; Sunjay Jude et al., filed Dec. 21, 2023.
Co-pending U.S. Appl. No. 18/743,583, inventor Nagendran; Monica, filed Jun. 14, 2024.
Co-pending U.S. Appl. No. 18/795,976, inventors Meer; Elliott et al., filed Aug. 6, 2024.
Co-pending U.S. Appl. No. 18/824,258, inventor Stott; Ryan Timothy, filed Sep. 4, 2024.
Co-pending U.S. Appl. No. 18/959,351, inventor Schnall-Levin; Michael, filed Nov. 25, 2024.
Co-pending U.S. Appl. No. 19/044,383, inventors Smibert; Peter et al., filed Feb. 3, 2025.

\* cited by examiner

SYSTEMS AND METHODS FOR NUCLEIC ACID PREPARATION

CROSS REFERENCE

This application is a continuation of U.S. application Ser. No. 15/896,543, filed Feb. 14, 2018, which is a continuation of PCT Application No. PCT/US2018/16926, filed Feb. 5, 2018, which claims priority to U.S. Provisional Patent Application No. 62/455,129, filed Feb. 6, 2017, all of which are entirely incorporated herein by reference for all purposes.

SEQUENCE LISTING

The instant application contains a Sequence Listing which has been filed electronically in ASCII format and is hereby incorporated by reference in its entirety. Said ASCII copy, created on Aug. 14, 2018, is named 43487-743_302_SL.txt and is 4,767 bytes in size.

BACKGROUND

Significant advances in analyzing and characterizing biological and biochemical materials and systems have led to unprecedented advances in understanding the mechanisms of life, health, disease and treatment. In particular, genomic sequencing is used to obtain biomedical information in diagnostics, prognostics, biotechnology, and forensics. Sample preparation is required before modern sequencing technologies such as Next Generation Sequencing (NGS) can be applied to nucleic acid samples. Such sample preparation can include amplification, unique identifier (or barcode) attachment, and nucleic acid length selection. One common step to prepare a set of nucleic acid samples for analysis is to construct a set of defined sequences embedded with barcodes. Thus, there is a need to find new methods to construct a set of barcoded nucleic acids for sequencing purposes.

In addition, various types of deoxyribonucleic acid (DNA) sequencing technologies available today involve the segmentation and processing of genomic materials into manageable sized barcoded fragments. Also common to the various types of sequencer technology is that each sequencer has an optimal range of insert sizes for the DNA samples. For example, short read sequencers, including Illumina sequencing platforms, perform best when the size distribution of DNA inserts is tightly controlled. Shorter DNA inserts result in wasted sequencing; longer inserts cause poor read quality.

Current methods for preparing DNA inserts of appropriate size include acoustic shearing and sonication, enzymatic methods of non-specific endonuclease cocktails and transposase tagmentation reactions, and Solid Phase Reversible Immobilization (SPRI) size selections. These are nonspecific solutions that may result in a wide distribution of various DNA sizes, and more mechanical/hands-on time for the operators of the sequencers. Therefore, it is desirable to control the size range of the DNA inserts for the set of barcoded fragments.

SUMMARY

As recognized herein, if fragment clusters are used in DNA sequencing, the average length of DNA inserts to be analyzed may determine the size of the corresponding cluster generated during cluster amplification. Short molecules (including adapter-dimers) cluster very efficiently, whereas fragments more than 700 base pair (bp) typically do not. Clusters that are too small or too big may not result in usable sequence reads, thereby affecting sequence capacity and coverage. For some sequencing applications, DNA inserts of a specific or uniform size may be important for sequence analysis. Consequently, it is advantageous to take the size of DNA inserts into consideration when designing or running DNA sequencing methods. DNA samples' diversity may be better preserved if the target DNA can be fragmented to a size distribution that is optimal for the sequencing read length favored by each specific sequencing application.

Provided herein are methods, systems and compositions for the preparation of nucleic acid samples, which may be employed for nucleic acid sequencing. Such samples may include, for example, a set of barcoded sequencing samples of target nucleic acids. The target nucleic acids may be amplified and fragmented during the preparation of the sequencing samples with a varying concentration of deoxycytidine triphosphate (dCTP) in the amplification reagent mixture.

Also provided here are methods, systems and composition for the control of the size range and/or distribution of insert sizes of sequencing analysis elements, for example, the sizes of DNA inserts in a set of barcoded sequencing samples of target nucleic acids. The barcoded fragments of target nucleic acids can be processed by non-naturally occurring CRISPR-Cas systems which selectively bind to barcoded fragments of target nucleic acids and cut the barcoded fragments into defined lengths.

In an aspect, the present disclosure provides a method for nucleic acid processing, comprising: (a) providing a template nucleic acid; (b) amplifying the template nucleic acid in the presence of deoxyuridine triphosphate (dUTP) or variant thereof to provide a complementary nucleic acid, wherein a concentration of the dUTP or variant thereof changes over the course of the amplification; (c) fragmenting the complementary nucleic acid into fragmented nucleic acids; (d) barcoding the fragmented nucleic acids to produce a first set of barcoded fragments comprising a plurality of first barcoded fragments; and (e) using a CRISPR-Cas to subject each of said plurality of first barcoded fragments to fragmentation to yield a second set of barcoded fragments comprising a plurality of second barcoded fragments.

In some embodiments of aspects provided herein, the method in (b) further comprises: (i) providing deoxynucleotide triphosphates (dNTPs), an N-mer, a polymerase, an enzyme substrate, and a first enzyme generating the dUTP or variant thereof; (ii) producing the dUTP or variant thereof from the enzyme substrate by the first enzyme; and (iii) amplifying the template nucleic acid with said polymerase, the dNTPs, the dUTP or variant thereof and the N-mer to provide the complementary nucleic acid comprising incorporated uracil or variant thereof. In some embodiments of aspects provided herein, the method in (c) further comprises: (i) providing a second enzyme excising the dUTP or variant thereof; and (ii) excising the incorporated uracil or variant thereof by the second enzyme, thereby providing nicks in the complementary nucleic acid to afford the fragmented nucleic acids.

In some embodiments of aspects provided herein, the second enzyme comprises a uracil excising enzyme. In some embodiments of aspects provided herein, the method in (d) further comprises: (i) providing a plurality of oligonucleotide barcode segments, and a third enzyme which extends nucleic acids; and (ii) extending the fragmented nucleic acids using the oligonucleotide barcode segments and the third enzyme to provide the first set of barcoded fragments. In some embodiments of aspects provided herein, the CRISPR-Cas comprises: (i) a Cas9 protein, (ii) a guide RNA capable of selectively coupling to a first target sequence in the first barcoded fragments, and (iii) an endonuclease, wherein the guide RNA binds the Cas9 protein, and wherein the Cas9 protein and the guide RNA do not naturally occur together.

In some embodiments of aspects provided herein, the CRISPR-Cas further comprises (iv) a spacer peptide linking the Cas9 protein and the endonuclease. In some embodiments of aspects provided herein, the spacer peptide is an alpha helix peptide or an unstructured peptide. In some embodiments of aspects provided herein, the Cas9 protein is catalytically inactive.

In some embodiments of aspects provided herein, the method in (e) further comprises: (i) subjecting the first barcoded fragments to the CRISPR-Cas under conditions that permit the guide RNA to selectively couple to the first barcoded fragments; and (ii) cleaving the first barcoded fragments by the endonuclease to make the double strand cuts. In some embodiments of aspects provided herein, the endonuclease is a non-specific nuclease. In some embodiments of aspects provided herein, the endonuclease is DNase I, *Aspergillus* nuclease S(1), *Serratia marcescens* nuclease, staphylococcal nuclease, micrococcal nuclease, or DNase A. In some embodiments, the fragmented nucleic acids are barcoded using nucleic acid barcode molecules attached to beads. In some embodiments, the beads are gel beads.

Another aspect of the present disclosure provides a method of preparing a set of sequencing samples, comprising: (a) providing a template nucleic acid, dNTPs, an N-mer, a polymerase, an enzyme substrate, a first enzyme generating dUTP or variant thereof, and a second enzyme excising dUTP or variant thereof; (b) producing dUTP or variant thereof from the enzyme substrate by the first enzyme; (c) amplifying the template nucleic acid with the polymerase, the dNTPs, the dUTP or variant thereof, and the N-mer to provide a complementary nucleic acid comprising incorporated uracil or variant thereof; and (d) excising the incorporated uracil or variant thereof by the second enzyme, thereby providing nicks in the complementary nucleic acid to afford fragmented nucleic acids.

In some embodiments of aspects provided herein, the first enzyme comprises a dCTP deaminase, and wherein the enzyme substrate comprises dCTP. In some embodiments of aspects provided herein, the first enzyme comprises a dCMP deaminase, and wherein the enzyme substrate comprises dCMP.

In some embodiments of aspects provided herein, the first enzyme further comprises a dUMP kinase. In some embodiments of aspects provided herein, the first enzyme comprises a dCDP deaminase, and wherein the enzyme substrate comprises dCDP. In some embodiments of aspects provided herein, the first enzyme further comprises a dUDP kinase. In some embodiments of aspects provided herein, the second enzyme comprises a uracil excising enzyme.

In some embodiments of aspects provided herein, in (c) the percentage of the incorporated uracil or variant thereof in the complementary nucleic acid increases over time. In some embodiments of aspects provided herein, the concentration of the dUTP or variant thereof changes over time, and wherein the change of the concentration of dUTP or variant thereof is caused by at least one factor selected from the group consisting of temperature, pH, concentration of the dCTP, concentration of inorganic phosphate, concentration of dTTP, and concentration of the first enzyme.

In some embodiments of aspects provided herein, the average length of the fragmented nucleic acids decreases over time. In some embodiments of aspects provided herein, the amplification in (c) is isothermal. In some embodiments of aspects provided herein, the polymerase is phi29 DNA polymerase.

In some embodiments of aspects provided herein, the method in (a) further comprises a plurality of beads comprising oligonucleotide adapter sequence segments. In some embodiments of aspects provided herein, the method in (d) further comprises (i) amplifying the nicked complementary nucleic acid to provide a double-stranded nucleic acid; and (ii) barcoding the double-stranded nucleic acid using a third enzyme capable of extending nucleic acids.

In some embodiments of aspects provided herein, the methods in (a)-(d) are performed in a discrete partition in the presence of at least one of the plurality of beads. In some embodiments of aspects provided herein, the plurality of beads is a pooled bead population. In some embodiments of aspects provided herein, the beads of the pooled bead population are co-partitioned with at least one from the group consisted of the template nucleic acid, the dNTPs, the dUTP or variant thereof, the N-mer, the polymerase, the first enzyme, the second enzyme, and wherein the partition optionally comprises a droplet in an emulsion.

In some embodiments of aspects provided herein, the third enzyme is selected from the group consisting of a ligating enzyme, a nucleic acid extension enzyme, and a transposase. In some embodiments of aspects provided herein, the ligating enzyme comprises an ATP independent enzyme. In some embodiments of aspects provided herein, the ligating enzyme is a topoisomerase or a T4 DNA ligase.

Still another aspect of the present disclosure provides a method of preparing a set of sequencing samples, comprising: providing a template nucleic acid, dNTPs, an N-mer, a polymerase, an enzyme substrate, a first enzyme generating dUTP or variant thereof, and a second enzyme excising dUTP or variant thereof; producing dUTP or variant thereof from the enzyme substrate by the first enzyme; amplifying the template nucleic acid with the polymerase, the dNTPs, the dUTP or variant thereof, and the N-mer to provide a complementary nucleic acid comprising incorporated uracil or variant thereof; and excising the incorporated uracil or variant thereof by the second enzyme, thereby providing nicks in the complementary nucleic acid to afford fragmented nucleic acids.

In some embodiments of aspects provided herein, the first enzyme comprises a dCTP deaminase, and wherein the enzyme substrate comprises dCTP. In some embodiments of aspects provided herein, the first enzyme comprises a dCMP deaminase, and wherein the enzyme substrate comprises dCMP. In some embodiments of aspects provided herein, the first enzyme further comprises a dUMP kinase. In some embodiments of aspects provided herein, the first enzyme comprises a dCDP deaminase, and wherein the enzyme substrate comprises dCDP. In some embodiments of aspects provided herein, the first enzyme further comprises a dUDP kinase.

In some embodiments of aspects provided herein, the second enzyme comprises a uracil excising enzyme. In some embodiments of aspects provided herein, in (c) the percentage of the incorporated uracil or variant thereof in the complementary nucleic acid increases over time.

In some embodiments of aspects provided herein, concentration of the dUTP or variant thereof changes over time, and wherein the change of the concentration of dUTP or variant thereof is caused by at least one factor selected from the group consisting of temperature, pH, concentration of the dCTP, concentration of inorganic phosphate, concentration of dTTP, and concentration of the first enzyme.

In some embodiments of aspects provided herein, the average length of the fragmented nucleic acids decreases over time. In some embodiments of aspects provided herein, the amplification in (c) is isothermal. In some embodiments of aspects provided herein, the polymerase is phi29 DNA polymerase.

In some embodiments of aspects provided herein, the method in (a) further comprises a plurality of beads comprising oligonucleotide adapter sequence segments. In some embodiments of aspects provided herein, the method in (d) further comprises (i) amplifying the nicked complementary nucleic acid to provide a double-stranded nucleic acid; and (ii) barcoding the double-stranded nucleic acid using a third enzyme capable of extending nucleic acids. In some embodiments of aspects provided herein, the steps of (a)-(d) of the method are performed in a discrete partition in the presence of at least one of the plurality of beads. In some embodiments of aspects provided herein, the plurality of beads is a pooled bead population. In some embodiments of aspects provided herein, the beads of the pooled bead population are co-partitioned with at least one from the group consisted of the template nucleic acid, the dNTPs, the dUTP or variant thereof, the N-mer, the polymerase, the first enzyme, the second enzyme, and wherein the partition optionally comprises a droplet in an emulsion.

In some embodiments of aspects provided herein, the third enzyme is selected from the group consisting of a ligating enzyme, a nucleic acid extension enzyme, and a transposase. In some embodiments of aspects provided herein, the ligating enzyme comprises an ATP independent enzyme. In some embodiments of aspects provided herein, the ligating enzyme is a topoisomerase or a T4 DNA ligase.

Another aspect of the present disclosure provides a method of preparing a set of barcoded sequencing samples, comprising: (a) providing a template nucleic acid, dNTPs, an N-mer, a polymerase, an enzyme substrate, a first enzyme generating dUTP or variant thereof, a second enzyme excising dUTP or variant thereof, a third enzyme extending nucleic acids, and a plurality of beads comprising oligonucleotide barcode sequence segments; (b) converting the enzyme substrate into dUTP or variant by the first enzyme; (c) amplifying the template nucleic acid with the polymerase, the dNTPs, the dUTP or variant thereof, and the N-mer to provide a complementary nucleic acid comprising incorporated uracil or variant thereof; (d) excising the incorporated uracil or variant thereof in the complementary nucleic acid by the second enzyme, thereby providing nicks in the complementary nucleic acid to yield a nicked complementary nucleic acid; (e) amplifying the nicked complementary nucleic acid to provide a set of amplified nucleic acids; (f) releasing the oligonucleotide barcode sequence segments from the plurality of beads; and (g) extending the amplified nucleic acids using the oligonucleotide barcode sequence segments and the third enzyme to provide the set of barcoded sequencing samples.

In some embodiments of aspects provided herein, the first enzyme comprises a dCTP deaminase, and wherein the enzyme substrate comprises dCTP. In some embodiments of aspects provided herein, the method further comprises adjusting activity of the dCTP deaminase by controlling at least one factor selected from the group consisting of temperature, pH, concentration of the dCTP, concentration of inorganic phosphate, concentration of dTTP, and concentration of the first enzyme.

In some embodiments of aspects provided herein, the dCTP deaminase is derived from *E. coli* or *M. jannaschii*. In some embodiments of aspects provided herein, the second enzyme comprises a uracil excising enzyme. In some embodiments of aspects provided herein, in (c) the percentage of the incorporated uracil or variant thereof in the complementary nucleic acid increases over time. In some embodiments of aspects provided herein, the amplification in (c) is isothermal.

In some embodiments of aspects provided herein, the polymerase is phi29 DNA polymerase. In some embodiments of aspects provided herein, the third enzyme is selected from the group consisting of a ligating enzyme, a nucleic acid extension enzyme and a transposase. In some embodiments of aspects provided herein, the ligating enzyme comprises an ATP independent enzyme. In some embodiments of aspects provided herein, in (d) the average length of the amplified nucleic acids decreases over time.

Still another aspect of the present disclosure provides a non-naturally occurring CRISPR-Cas system, comprising: (a) a Cas protein; (b) a guide ribonucleic acid (RNA) capable of selectively coupling to a first target sequence; (c) an endonuclease; and (d) a spacer peptide linking the Cas protein and the endonuclease; wherein the guide RNA binds the Cas protein, and wherein the Cas protein and the guide RNA do not naturally occur together.

In some embodiments of aspects provided herein, the CRISPR-Cas system is a Type II CRISPR-Cas system. In some embodiments of aspects provided herein, the Cas protein is catalytically inactive. In some embodiments of aspects provided herein, the Cas protein is Cas9 protein, CasX protein, or CasY protein. In some embodiments of aspects provided herein, the guide RNA comprises a chimeric RNA that includes a guide sequence and a tracr sequence.

In some embodiments of aspects provided herein, the first target sequence comprises at least part of an adapter sequence of a fragmented DNA. In some embodiments of aspects provided herein, the adapter sequence is P5 adapter or P7 adapter.

In some embodiments of aspects provided herein, the spacer peptide is an alpha helix peptide or an unstructured peptide. In some embodiments of aspects provided herein, the endonuclease is a non-specific nuclease. In some embodiments of aspects provided herein, the endonuclease is DNase I, *Aspergillus* nuclease S(1), *Serratia marcescens* nuclease, staphylococcal nuclease, micrococcal nuclease, or DNase A.

Another aspect of the present disclosure provides a method for preparing a set of nucleic acid molecules, comprising: (a) providing a plurality of nucleic acids of varying lengths, wherein each of the nucleic acids of varying lengths comprises a first target sequence; (b) providing a non-naturally occurring CRISPR-Cas complex which comprises (i) a Cas protein, (ii) a guide RNA capable of selectively coupling to the first target sequence, and (iii) an endonuclease, wherein the guide RNA binds the Cas protein, and wherein the Cas protein and the guide RNA do not naturally occur together; (c) bringing the plurality of the nucleic acids of varying lengths in contact with the CRISPR-Cas complex under conditions that permit the guide RNA to selectively couple to the first target sequence of the nucleic acids of varying lengths; and (d) cleaving the nucleic acids of varying lengths by the endonuclease, thereby providing the set of nucleic acid molecules.

In some embodiments of aspects provided herein, the CRISPR-Cas complex in (b) further comprises (iv) a spacer peptide linking the Cas protein and the endonuclease. In some embodiments of aspects provided herein, the spacer peptide is an alpha helix peptide or an unstructured peptide. In some embodiments of aspects provided herein, the Cas protein is catalytically inactive. In some embodiments of aspects provided herein, the Cas protein is Cas9 protein, CasX protein, or CasY protein. In some embodiments of aspects provided herein, the guide RNA comprises a chimeric RNA that includes a guide sequence and a tracr sequence. In some embodiments of aspects provided herein, the first target sequence comprises at least part of an adapter sequence of a fragmented DNA. In some embodiments of aspects provided herein, the adapter sequence is P5 adapter or P7 adapter.

In some embodiments of aspects provided herein, the endonuclease is a non-specific nuclease. In some embodiments of aspects provided herein, the endonuclease is DNase I, *Aspergillus* nuclease S(1), *Serratia marcescens* nuclease, staphylococcal nuclease, micrococcal nuclease, or DNase A.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG" and "FIGs" herein), of which:

DETAILED DESCRIPTION

Figure 1:
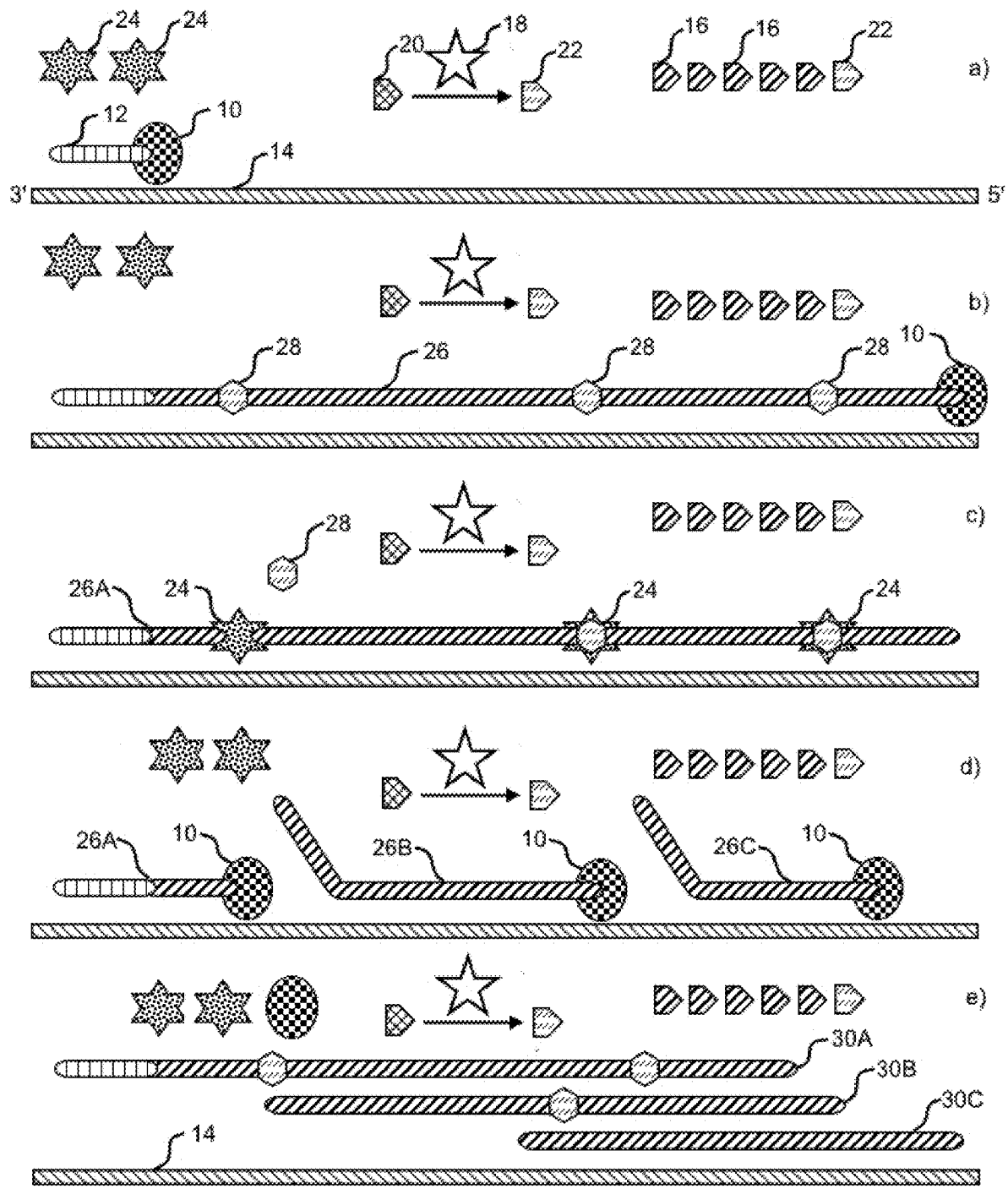
FIG. 1 is a diagram illustrating a process of preparing amplified fragments from a target nucleic acid template. Panel a) of FIG. 1 shows a DNA polymerase can initiate an amplification on a target strand in the presence of a dCTP deaminase. Panel b) of FIG. 1 depicts the DNA polymerase extending a copied strand comprising uracils. Panel c) of FIG. 1 illustrates uracil excising enzyme creating shorter copied strands. Panel d) shows the DNA polymerase continuing amplification of shorter copied strands. Panel e) depicts released amplified fragments.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

As used in this specification and the appended claims, the singular forms "a," "an" and "the" include plural referents unless the context clearly dictates otherwise. Thus, for example, reference to "a molecule" includes a plurality of such molecules, and the like.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed samples or sets) across multiple and/or remote physical compartments. For example, a physical compartment may comprise a plurality of virtual compartments.

As used herein, the terms "bell-shape" and "bell-shaped" generally refer to a symmetric, unimodal (e.g., one bump at the center) shape tapering off to the sides. A bell-shaped distribution may also be a Normal distribution or Gaussian distribution. A Normal distribution may be denoted by $N(\mu,\sigma)$ where $\mu$ and $\sigma$ are the mean and standard deviation of the Normal distribution, respectively, and they are parameters. A tighter bell-shape is a Normal distribution with a smaller a value.

As used herein, the term "CRISPR" generally refers to clustered regularly interspaced short palindromic repeat. As used herein, the term "Cas" generally refers to a CRISPR associated protein. As used herein, the term "Cas9" or "Cas9 nuclease" generally refers to an RNA-guided nuclease comprising a Cas9 protein, or a fragment thereof (e.g., a protein comprising an active or inactive DNA cleavage domain of Cas9, and/or the guide RNA binding domain of Cas9). Cas9 orthologs have been described in various species, including, but not limited to, *S. pyogenes* and *S. thermophilus*. Additional suitable Cas9 nucleases and sequences may include Cas9 sequences from the organisms and loci disclosed in Chylinski, K., "The tracrRNA and Cas9 families of type II CRISPR-Cas immunity systems," *RNA Biology* (2012) 10(5):726-37, 2012, which is entirely incorporated herein by reference. In some cases, a Cas9 nuclease has an inactive (e.g., an inactivated) DNA cleavage domain.

As used herein, the term "CRISPR-Cas," "CRISPR-Cas nuclease" or "CRISPR-Cas protein" generally refers to any type II nucleases (wild type or modified version thereof) associated with CRISPR, including, for example, the CRISPR-Cas protein in Archaea (made up of about 950 amino acids), the CRISPR-Cas protein in *Streptococcus. aureus* (made up of about 1,053 amino acids, also known as saCas9), the CRISPR-Cas protein in *Staphylococcus pyogenes* (made up of about 1,368 amino acids, also known as spCas9), Cpf1 protein in *Prevotella* and *Francisella* (made up of about 1,200 to 1,300 amino acids), CRISPR-CasX protein in Plantomycetes and Deltaproteobacteria (made up of about 980 amino acids), and CRISPR-CasY protein from Candidate Phyla Radiation (made up of about 1,200 amino acids). See, Burstein, D. et al., "New CRISPR-Cas systems from uncultivated microbes," *Nature* (2016), doi:10.1038/nature21059, which is entirely incorporated herein by reference.

The term "fragment" as used herein generally refers to a fraction or segment of an original DNA sequence or RNA sequence. A fragment may be generated by various approaches, such as enzymatic degradation or mechanical degradation (e.g., sonication) or a nucleic acid (e.g., DNA or RNA) sample.

The term "mutation" as used herein generally refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) may be used, such as, for example, Green and Sambrook, *Molecular Cloning: A Laboratory Manual* 4$^{th}$ ed., Cold Spring Harbor Laboratory Press, Cold Spring Harbor, N.Y., 2012, which is entirely incorporated herein by reference.

The term "nuclease," as used herein, generally refers to an agent, for example a protein, capable of cleaving a phosphodiester bond connecting nucleotide residues in a nucleic acid molecule. In some cases, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain.

The terms "protein," "peptide," and "polypeptide," as used herein, are used interchangeably, and generally refer to a polymer of amino acid residues linked together by peptide (amide) bonds. These terms generally refer to a protein, peptide, or polypeptide of any size, structure, or function. Typically, a protein, peptide, or polypeptide can be at least three amino acids long. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. Proteins provided herein may be produced by various approaches. For example, the proteins provided herein may be produced via recombinant protein expression and purification. Methods for recombinant protein expression and purification may include those described by Green and Sambrook, *Molecular Cloning: A Laboratory Manual* 4$^{th}$ ed., Cold Spring Harbor Laboratory Press, Cold Spring Harbor, N.Y., 2012, which is entirely incorporated herein by reference.

The term "target nucleic acid" as used herein generally refers to the nucleic acid or nucleic acid fragment targeted for detection and/or sequencing analysis. Sources of target nucleic acids may be isolated from organisms, including mammals, or pathogens to be identified, including viruses and bacteria. Additionally target nucleic acids can also be from synthetic sources. Target nucleic acids may be or may not be amplified via standard replication/amplification procedures to produce nucleic acid sequences.

The term "nucleic acid sequence" or "nucleotide sequence" as used herein generally refers to nucleic acid molecules with a given sequence of nucleotides, of which it may be desired to know the presence or amount. The nucleotide sequence can comprise ribonucleic acid (RNA) or DNA, or a sequence derived from RNA or DNA. Examples of nucleotide sequences are sequences corresponding to natural or synthetic RNA or DNA including genomic DNA and messenger RNA. The length of the sequence can be any length that can be amplified into nucleic acid amplification products, or amplicons, for example, up to about 20, 50, 100, 200, 300, 400, 500, 600, 700, 800, 1,000, 1,200, 1,500, 2,000, 5,000, 10,000 or more than 10,000 nucleotides in length, or at least about 20, 50, 100, 200, 300, 400, 500, 600, 700, 800, 1,000, 1,200, 1,500, 2,000, 5,000, 10,000 or 10,000 nucleotides in length.

The term "template" as used herein generally refers to individual polynucleotide molecules from which another nucleic acid, including a complementary nucleic acid strand, can be synthesized by a nucleic acid polymerase. In addition, the template can be one or both strands of the polynucleotides that are capable of acting as templates for template-dependent nucleic acid polymerization catalyzed by the nucleic acid polymerase. Use of this term should not be taken as limiting the scope of the present disclosure to polynucleotides which are actually used as templates in a subsequent enzyme-catalyzed polymerization reaction. The template can be an RNA or DNA. The template can be cDNA corresponding to an RNA sequence. The template can be DNA.

As used herein, "amplification" of a template nucleic acid generally refers to a process of creating (e.g., in vitro) nucleic acid strands that are identical or complementary to at least a portion of a template nucleic acid sequence, or a universal or tag sequence that serves as a surrogate for the template nucleic acid sequence, all of which are only made if the template nucleic acid is present in a sample. Typically, nucleic acid amplification uses one or more nucleic acid polymerase and/or transcriptase enzymes to produce multiple copies of a template nucleic acid or fragments thereof, or of a sequence complementary to the template nucleic acid or fragments thereof. In vitro nucleic acid amplification techniques are may include transcription-associated amplification methods, such as Transcription-Mediated Amplification (TMA) or Nucleic Acid Sequence-Based Amplification (NASBA), and other methods such as Polymerase Chain Reaction (PCR), Reverse Transcriptase-PCR (RT-PCR), Replicase Mediated Amplification, and Ligase Chain Reaction (LCR).

As used herein, the term "isothermal amplification" generally refers to an amplification reaction that is conducted at a substantially constant temperature. The isothermal portion of the reaction may be preceded or followed by one or more operations at a variable temperature, for example, a first denaturation step and a final heat inactivation step or cooling step. It will be understood that this definition does not exclude certain, in some cases small, variations in temperature but is rather used to differentiate the isothermal amplification techniques from other amplification techniques that may rely on "cycling temperatures" in order to generate the amplified products. Isothermal amplification differs from PCR, for example, in that the latter relies on cycles of denaturation by heating followed by primer hybridization and polymerization at a lower temperature. Isothermal amplification can rely on chemistries, including but not limited to, loop-mediated isothermal amplification (LAMP), strand displacement amplification (SDA), helicase-dependent amplification (HDA), and nicking enzyme amplification reaction (NEAR).

As used herein, the term "Y-adapter" generally refers to an adapter with two nucleic acid strands (e.g., DNA strands), part of which are not complementary to each other, thereby forming a fork of single-stranded DNA arms. The non-complementary arms of the Y-adapter can contain different elements such as identifiers or barcodes, sequencing adapters, primer binding sites etc. The bottom end of the Y-shape is double stranded (i.e. contains complementary strands). As used herein, Y-adapter and Y-shaped adapter generally refer to the same. The attachment of the Y-adapters to DNA fragments can be effected by ligating the Y-adapters to one or both 5'- or 3'-ends of the DNA fragments, and then optionally carrying out an initial primer extension reaction, in which extension products complementary to the immobilized oligonucleotides can be formed. This operation can optionally comprise an amplification step for multiplying the adapter-fragment-constructs. The forked or Y-adapters can be ligated to either end or both ends of the DNA fragments by a DNA ligase. The separate strands of the double-stranded part are ligated to each end of a target sequence and a primer pair is added to the ligated DNA. One primer anneals to the target sequence in an adapter at one end of the target DNA and the other primer in the pair anneals to the target sequence on the complementary strand of the adapter at the other end of the target DNA. Y-shaped adapters have been disclosed in U.S. Pat. No. 7,741,46, which is entirely incorporated herein by reference. The term "about" or "nearly" as used herein generally refers to within +/−15%, 10%, 9%, 8%, 7%, 6%, 5%, 4%, 3%, 2%, or 1% of the designated amount.

Sequence information of nucleic acids may be the foundation to improve people's lives through clinical approaches or by material approaches. (See, Ansorge, W., "Next-generation DNA sequencing techniques," *New Biotech.* (2009) 25(4):195-203, which is entirely incorporated herein by reference). Several parallel DNA sequencing platforms have been available on the market. The availability of NGS accelerates biological and biomedical research enables the comprehensive analysis of genomes, transcriptomes and interactomes. (See, Shendure, J. and Ji, H., "Next-generation DNA sequencing," *Nature Biotech.* (2008) 26:1135-45, which is entirely incorporated herein by reference). One particular challenge faced by researchers in the NGS filed is a more robust protocol for generating a set of sequencing samples, for example, a set of barcoded samples.

Commonly used and commercially available NGS sequencing platforms include the Illumina Genome Analyzer, the Roche (454) Genome Sequencer, the Life Technologies SOLiD platform, and real-time sequencers such as Pacific Biosciences. Most of these platforms require the construction of a set of DNA fragments from a biological sample. The DNA fragments are, in most cases, flanked by platform-specific adapters. Common methods for constructing such a set of DNA fragments can include operations, such as, fragmenting sample DNA's, polishing ends of fragments, ligating adapter sequences to ends, selecting fragment size, amplifying fragments by PCR, and quantitating the final sample products for sequencing. The insert size or the size of the target DNA fragments in the final set of sequencing samples is a key parameter for NGS analysis.

Sample Preparation Using Priming Free Amplification

The present disclosure provides methods for constructing nucleic acid samples or barcoded nucleic acid samples. In some cases, such methods involve priming-free amplification.

Priming free amplification may be performed to prepare a set of sequencing samples by polymerization at nicking sites in the absence of primers (priming free amplification). Shown in FIG. 1, in a priming free amplification, there are several enzymes involved in the sample preparation process. As shown in panel (a) in FIG. 1, a DNA polymerase 10, for example, a phi29 DNA polymerase (New England BIO-LABS® Inc., Ipswich, Mass.), can work with an N-mer 12 in the initiation stage and perform an isothermal amplification on a target strand 14 in the presence of reagents deoxynucleotide triphosphates (dNTPs) 16. In addition, a deoxycytidine triphosphate (dCTP) generating enzyme 18 can convert an enzyme substrate 20 to a reagent deoxyuridine triphosphate (dUTP) 22. An example of such a reaction can be a dCTP deaminase catalyzed conversion of dCTP to produce dUTP 22. The reagent dUTP 22, in turn, can be processed by the DNA polymerase 10 in the amplification process. Further, a uracil excising enzyme 24 can be present as well, whose function will be explained vide infra.

Thus, as the amplification continues, as shown in panel (b) in FIG. 1, dUTP 22 together with dNTPs 16 can be processed by the DNA polymerase 10 to extend a copied strand 26 using the target strand 14 as a template. As a result, uracils 28 can be incorporated into the copied strand 26. The uracil excising enzyme 24, as shown in panel (c) in FIG. 1, can generate a single nucleotide gap at the location of the incorporated uracil 28 in the copied strand 26, but creates no such gap in the target strand 14. Consequently, the copied strand 26 can be fragmented into shorter copied strands 26A, 26B, and 26C, as shown in panel (d) in FIG. 1. In particular, the shorter copied strand 26A may comprise the N-mer 12. However, the shorter copied strands 26B and 26C may not comprise the N-mer 12. Then the DNA polymerase 10 can engage with the shorter copied strands 26A, 26B, and 26C at the 3' end of the nicking sites for continuing amplifications in a priming independent amplification process over the target strand 14.

In the end, amplified fragments 30A, 30B and 30C can be released from the target strand 14, as shown in panel (e) in FIG. 1. Some amplified fragments, such as 30A and 30B, can contain incorporated uracils 28, which are substrates for the uracil excising enzyme 24. Therefore, some amplified fragments, for example, 30A and 30B, can be further processed to afford shorter fragments thereof. The released target strand 14, and/or amplified fragments 30A-30C, can start another round of amplification process similar to what has been shown vide supra.

Although FIG. 1 displays panels (a)-(e), the process illustrated in FIG. 1 can be performed simultaneously in the presence of all the required reagents or in selected operations when certain reagents are not available.

In some cases, dUTP reagents can be supplemented to the amplification reaction of target nucleic acid, for example, genomic nucleic acid, in micro-emulsion partitions when using phi29 DNA polymerase to conduct isothermal amplification. Coupled with a uracil excising enzyme in the same partition, the incorporated uracils in the amplified strand may provide nicking sites as initiation sits for phi29 DNA polymerase. The initial dUTP reagents in the isothermal amplification may be supplied directly during partitioning or may be produced in situ by an enzyme-catalyzed process within the partition. By relying on the enzymatic conversion to produce dUTP in situ, the concentration of dUTP in the same partition can be varied over the duration of the amplification reaction within the partition.

The advantages of using an enzymatic route to supplement dUTP may be as follows. If the supply of dUTP is solely from the initial source when the partition is formed, due to the usage of dUTP in amplification reaction, the concentration of dUTP may decrease over the course of amplification reaction. In addition, the relative ratio of uracil base vs. regular thymine base in the amplified products may not increase. Hence, to increase the concentration of dUTP over time may require constant addition of fresh dUTP into the partitions, which may become a problem in operation. Furthermore, due to the nature of the isothermal amplification process, it may be beneficial to have relatively low concentration of dUTP at early reaction time, which may lead to longer amplified/copied strands to be made in the beginning stage of the amplification. It may also be beneficial to have relatively high concentration of dUTP near the end of amplification, which may result in shorter amplified fragments due to more incorporation of uracil with the amplified strands. These shorter fragments of amplified nucleic acid can be barcoded for further sequencing analysis. Therefore, there is a need to vary the concentration of dUTP over the course of the isothermal amplification process.

Deoxycytidine triphosphate (dCTP) deaminase can catalyze the deamination of dCTP to afford deoxyuridine triphosphate (dUTP) and ammonia. dCTP deaminase is found in *E. coli, M. jannaschii*, and other organisms. The *E. coli*-derived enzyme may be active near neutral pH, and may be inhibited by inorganic phosphate and deoxythymidine triphosphate (dTTP). Johansson, E., et al., "Structures of dCTP deaminase from *Escherichia coli* with bound substrate and product: reaction mechanism and determinants of mono- and bifunctionality for a family of enzymes," *J. Biol. Chem.* (2005) 280(4):3051-9, which is entirely incorporated herein by reference. The inclusion of dCTP deaminase in the amplification reaction mixture in the partition can increase the concentration of dUTP, or the relative ratio of dUTP to dTTP, over time at a controllable rate. A low initial dUTP concentration can push amplification toward multiple displacement amplification on the template nucleic acid. Over time, dCTP deaminase can convert more and more dCTP present in the reaction mixture to reagent dUTP, thereby increasing the incorporation of uracil-containing base into the amplified nucleic acid copies to produce more nicking site in and shorter fragments of copied strands of nucleic acid template. At the end of the amplification process, the reaction products can become shorter than in the beginning phase of the process and these shorter fragments can be available for the ensuing barcoding operation.

dCTP deaminase activity can be tailored by, for example, adjusting the reaction temperature, pH, dCTP concentration, inorganic phosphate concentration, and dTTP concentration. These factors, along with dCTP deaminase concentration, can allow the dUTP concentration in the amplification reaction to be controlled over time. For example, pH can be adjusted by the addition of base or acid; temperature can be increased or lowed; dCTP can be added to or removed from the reagent mixture; inorganic phosphate can be added to or removed from the reagent mixture; dTTP can be added to or removed from the reaction mixture; and dCTP deaminase can be added to or removed from the reaction mixture. Other conditions to vary the concentration of dUTP over time are possible.

Furthermore, dCTP deaminase can be genetic engineered to relieve inhibition by phosphate, dTTP, or other small molecules in the partition. In addition, dCTP deaminase can be engineered to change its thermal stability profile, among other properties.

Other ways to produce dUTP in situ over the course of the amplification process can include, for example, supplying the reaction mixture with deoxycytidine monophosphate (dCMP) and a dCMP deaminase to convert dCMP to deoxyuridine monophosphate (dUMP), followed by the action of a kinase to convert dUMP to dUTP; or supplying the reaction mixture with deoxycytidine diphosphate (dCDP) and a dCDP deaminase to phosphorylate dCDP to deoxyuridine diphosphate (dUDP), followed by the action of another kinase to convert dUDP to dUTP.

By varying the concentration of dUTP over time during the amplification of a template strand, the percentage of incorporated uracil-containing base in the replicates can vary. In some cases, the percentage of incorporated uracil-containing base in the replicate can increase over time. As used herein, the percentage of incorporated uracil generally refers to the average ratio of the total number of incorporated uracil-containing bases over the total number of bases in replicates. The average interval between adjacent incorporated uracil-containing bases within a replicate can be another indicator of the percentage of incorporated uracil-containing base in the replicate. The higher the percentage of incorporated uracil-containing base, the shorter the average interval between adjacent incorporated uracil-containing bases.

Sequencing samples produced according to the present disclosure can provide sequencing results, for example, whole genome sequencing results, when coupled with sequencing methods or systems. The efficiency of the disclosed methods can be optimized by changing some reaction conditions or by varying the reagents added to the amplification process, as shown herein.

The sequencing samples produced according to the present disclosure can be employed in nucleic acid analysis applications, such as, for example, nucleic acid sequencing applications. A method often used in DNA sample constructions is called emulsion PCR (E-PCR) with microbeads. E-PCR method is used by Roche's 454 (Margulies, et al., "Genome Sequencing in Microfabricated High-density Picolitre Reactors," *Nature* (2005) 437(7057):376-80) and Life Technologies' SOLiD (Valouev, et al., "A High-resolution, Mucleosome Position Map of C. *Elegans* Reveals a Lack of Universal Sequence-dictated Positioning," *Genome Res.* (2008) 18(7):1051-63) and Ion Torrent (Rothberg, et al., "An Integrated Semiconductor Device Enabling Non-optical Genome Sequencing," *Nature* (2011) 475(7356):348-52) platforms, all of which are entirely incorporated herein by reference. E-PCR can require performing PCR on billions of microbeads, each isolated in its own emulsion droplet, followed by emulsion breakup, template enrichment, and bead deposition before sequencing. The methods and systems disclosed in the present disclosure can be applicable in E-PCR.

Sequencing Samples Construction Using Barcodes

This disclosure also provides methods, systems and compositions useful in the processing of sample materials, for example, nucleic acids samples, through the controlled delivery of reagents to subsets of sample components, followed by analysis of those sample components employing, in part, the delivered reagents. In many cases, the methods and compositions can be employed for sample processing, particularly for nucleic acid analysis applications, generally, and nucleic acid sequencing applications, in particular. Included within this disclosure are bead compositions that include diverse sets of reagents, such as diverse sets of beads attached to large numbers of oligonucleotides containing barcode sequences, and methods of making and using the same. Methods, systems and composition, described in U.S. Patent Publication Nos. 2015/0376609 and 2016/0257984, all of which are hereby incorporated herein by reference in its entirety for all purposes, can process samples materials, including nucleic acids samples, by using a set of beads with oligonucleotide barcodes.

The methods, systems and composition of this present disclosure may be used with bead or particle, including, for example, gel beads and other types of beads. Beads may serve as a carrier for reagents that are to be delivered in accordance with the methods described herein. In some cases, these beads may provide a surface to which reagents are releasably attached, or a volume in which reagents are entrained or otherwise releasably partitioned. These reagents may then be delivered in accordance with methods described herein, for example, in the controlled delivery of reagents into discrete partitions. A variety of different reagents or reagent types may be associated with the beads, when delivering such reagents to a partition. Non-limiting examples of such reagents delivered include, e.g., enzymes, polypeptides, antibodies or antibody fragments, labeling reagents, e.g., dyes, fluorophores, chromophores, etc., nucleic acids, polynucleotides, oligonucleotides, and any combination of two or more of the foregoing. In some cases, the beads may provide a surface upon which to synthesize or attach oligonucleotide sequences. Various entities including oligonucleotides, barcode sequences, primers, adaptors, linkers, and/or cross-linkers may be associated with the outer surface of a bead. In the case of porous beads, an entity may be associated with both the outer and inner surfaces of a bead. The entities may be attached directly to the surface of a bead (e.g., via a covalent bond, ionic bond, van der Waals interactions, etc.), may be attached to other oligonucleotide sequences attached to the surface of a bead (e.g. adaptor or primers), may be diffused throughout the interior of a bead and/or may be combined with a bead in a partition (e.g. fluidic droplet). In some cases, the oligonucleotides can be covalently attached to sites within the polymeric matrix of the bead and are therefore present within the interior and exterior of the bead. In some cases, an entity such as a cell or nucleic acid may be encapsulated within a bead. Other entities including amplification reagents (e.g., PCR reagents, primers) may also be diffused throughout the bead or chemically-linked within the interior (e.g., via pores, covalent attachment to polymeric matrix) of a bead.

Beads may serve to localize entities or samples. In some cases, entities (e.g. oligonucleotides, barcode sequences, primers, cross-linkers, adaptors and the like) may be associated with the outer and/or an inner surface of the bead. In some cases, entities may be located throughout the bead. In some cases, the entities may be associated with the entire surface of a bead or with at least half the surface of the bead.

Beads may serve as a support on which to synthesize oligonucleotide sequences. In some cases, synthesis of an oligonucleotide may comprise a ligation step. In some cases, synthesis of an oligonucleotide may comprise ligating two smaller oligonucleotides together. In some cases, a primer extension or other amplification reaction may be used to synthesize an oligonucleotide on a bead via a primer attached to the bead. In such cases, a primer attached to the bead may hybridize to a primer binding site of an oligonucleotide that also contains a template nucleotide sequence. The primer can then be extended by a primer extension reaction or other amplification reaction, and an oligonucleotide complementary to the template oligonucleotide can thereby be attached to the bead. In some cases, a set of identical oligonucleotides associated with a bead may be ligated to a set of diverse oligonucleotides, such that each identical oligonucleotide is attached to a different member of the diverse set of oligonucleotides. In some cases, a set of diverse oligonucleotides associated with a bead may be ligated to a set of identical oligonucleotides. In some cases, the set of diverse oligonucleotides may be a set of fragments of a target nucleic acid. In some cases, the set of identical oligonucleotides may be adaptors or nucleic acids comprising barcodes.

Methods of making beads can generally include, for example, combining bead precursors (such as monomers or polymers), primers or adaptors, and cross-linkers in an aqueous solution, combining said aqueous solution with an oil phase, sometimes using a microfluidic device or droplet generator, and causing water-in-oil droplets to form.

In some cases, a catalyst, such as an accelerator and/or an initiator, can be added before or after droplet formation. In some cases, initiation can be achieved by the addition of energy, such as, for example, via the addition of heat or light (e.g., UV light). A polymerization reaction of bead precursors in the droplet can occur to generate a bead.

In some cases, the bead can be covalently linked to one or more copies of an oligonucleotide (e.g., primer or adaptor) to become functionalized. Additional nucleic acid sequences can be attached to the functionalized beads using a variety of methods. In some cases, the functionalized beads may be combined with a template oligonucleotide (e.g., a barcode) and partitioned such that on average one or fewer template oligonucleotides may occupy the same partition as a functionalized bead. While the partitions can be any of a variety of different types of partitions, e.g., wells, microwells, tubes, vials, microcapsules, etc., in some cases, the partitions can be droplets (e.g., aqueous droplets) within an emulsion.

Beads may be made in a device or beads (or other types of partitions) may be combined in a device with samples, e.g., for co-partitioning sample components. The device may be a microfluidic device (e.g., a droplet generator). In some cases, the device may be formed from a material selected from the group consisting of fused silica, soda lime glass, borosilicate glass, poly (methyl methacrylate) PMMA, PDMS, sapphire, silicon, germanium, cyclic olefin copolymer, polyethylene, polypropylene, polyacrylate, polycarbonate, plastic, thermosets, hydrogels, thermoplastics, paper, elastomers, and combinations thereof.

The device may comprise fluidic channels for the flow of fluids. In some cases, a device may comprise one or more fluidic input channels (e.g., inlet channels) and one or more fluidic outlet channels. In some cases, the microfluidic device may be utilized to form beads by forming a fluidic droplet comprising one or more gel precursors, one or more cross-linkers, optionally an initiator, and optionally an aqueous surfactant.

The microfluidic device may be used to combine beads (e.g., barcoded beads or other type of first partition) with sample (e.g., a sample of nucleic acids) by forming a fluidic droplet (or other type of second partition) comprising both the beads and the sample. The fluidic droplet may have an aqueous core surrounded by an oil phase, such as, for example, aqueous droplets within a water-in-oil emulsion. The oil may further comprise a surfactant and/or an accelerator. The fluidic droplet may contain one or more barcoded beads, a sample, amplification reagents, and a reducing agent. In some cases, the fluidic droplet may include one or more of water, nuclease-free water, acetonitrile, beads, gel beads, polymer precursors, polymer monomers, polyacrylamide monomers, acrylamide monomers, degradable cross-linkers, non-degradable cross-linkers, disulfide linkages, acrydite moieties, PCR reagents, primers, polymerases, barcodes, polynucleotides, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, probes, dyes, organics, emulsifiers, surfactants, stabilizers, polymers, aptamers, reducing agents, initiators, biotin labels, fluorophores, buffers, acidic solutions, basic solutions, light-sensitive enzymes, pH-sensitive enzymes, aqueous buffer, oils, salts, detergents, ionic detergents, non-ionic detergents, and the like. The composition of the fluidic droplet may vary depending on the particular processing needs. The fluidic droplets may be of uniform size or heterogeneous size.

The device may comprise one or more intersections of two or more fluid input channels. For example, the intersection may be a fluidic cross. The fluidic cross may comprise two or more fluidic input channels and one or more fluidic outlet channels. In some cases, the fluidic cross may comprise two fluidic input channels and two fluidic outlet channels. In some cases, the fluidic cross may comprise three fluidic input channels and one fluidic outlet channel. In some cases, the fluidic cross may form a substantially perpendicular angle between two or more of the fluidic channels forming the cross.

A microfluidic device may comprise a first and second input channels that meet at a junction that is fluidly connected to an output channel. In some cases, the output channel may be, for example, fluidly connected to a third input channel at another junction. In some cases, a fourth input channel may be included and may intersect the third input channel and the outlet channel at still another junction. In some cases, a microfluidic device may comprise first, second, and third input channels, wherein the third input channel may intersect the first input channel, the second input channel, or a junction of the first input channel and the second input channel.

The microfluidic device may be used to generate gel beads from a liquid. For example, in some cases, an aqueous fluid comprising one or more gel precursors, one or more cross-linkers and optionally an initiator, optionally an aqueous surfactant, and optionally an alcohol within a fluidic input channel may enter a fluidic cross. Within a second fluidic input channel, an oil with optionally a surfactant and an accelerator may enter the same fluidic cross. Both aqueous and oil components may be mixed at the fluidic cross to form aqueous fluidic droplets within the continuous oil phase. Gel precursors within fluidic droplets exiting the fluidic cross may polymerize to form beads.

The microfluidic device may be used to combine sample with beads (e.g., a set of barcoded beads) as well as an agent capable of degrading the beads (e.g., reducing agent if the beads are linked with disulfide bonds). In some cases, a sample (e.g., a sample of nucleic acids) may be provided to a first fluidic input channel that is fluidly connected to a first fluidic cross (e.g., a first fluidic junction). Pre-formed beads (e.g., barcoded beads, degradable barcoded beads) may be provided to a second fluidic input channel that is also fluidly connected to the first fluidic cross, where the first fluidic input channel and second fluidic input channel meet. The sample and beads may be mixed at the first fluidic cross to form a new mixture (e.g., an aqueous mixture). In some cases, a reducing agent may be provided to a third fluidic input channel that is also fluidly connected to the first fluidic cross and meets the first and second fluidic input channels at the first fluidic cross. The reducing agent can then be mixed with the beads and the sample in the first fluidic cross. In some cases, the reducing agent may be premixed with the sample and/or the beads before entering the microfluidic device such that it is provided to the microfluidic device through the first fluidic input channel with the sample and/or through the second fluidic input channel with the beads. In some cases, no reducing agent may be added.

The sample and bead mixture may exit the first fluidic cross through a first outlet channel that is fluidly connected to the first fluidic cross (and, thus, any fluidic channels forming the first fluidic cross). The mixture may be provided to a second fluidic cross (e.g., a second fluidic junction) that is fluidly connected to the first outlet channel. In some cases, an oil (or other suitable immiscible) fluid may enter the second fluidic cross from one or more separate fluidic input channels that are fluidly connected to the second fluidic cross (and, thus, any fluidic channels forming the cross) and that meet the first outlet channel at the second fluidic cross. In some cases, the oil (or other suitable immiscible fluid) may be provided in one or two separate fluidic input channels fluidly connected to the second fluidic cross (and, thus, the first outlet channel) that meet the first outlet channel and each other at the second fluidic cross. The oil, and the sample and bead mixture, may be mixed at the second fluidic cross. This mixing may partition the sample and bead mixture into a plurality of fluidic droplets (e.g., aqueous droplets within a water-in-oil emulsion), in which at least a subset of the droplets may encapsulate a barcoded bead (e.g., a gel bead). The fluidic droplets that formed may be carried within the oil through a second fluidic outlet channel exiting from the second fluidic cross. In some cases, fluidic droplets exiting the second outlet channel from the second fluidic cross may be partitioned into wells for further processing.

In many cases, it may be desirable to control the occupancy rate of resulting droplets (or second partitions) with respect to beads (or first partitions). An example of such control is described in U.S. Patent Publication No. 2015/0292988, the full disclosure of which is incorporated herein by reference in its entirety for all purposes. In general, the droplets (or second partitions) can be formed such that at least 50%, 60%, 70%, 80%, 90% or more droplets (or second partitions) contain no more than one bead (or first partition). Additionally, or alternatively, the droplets (or second partitions) can be formed such that at least 50%, 60%, 70%, 80%, 90% or more droplets (or second partitions) include exactly one bead (or first partition). In some cases, the resulting droplets (or second partitions) may each comprise, on average, at most about one, two, three, four, five, six, seven, eight, nine, ten, eleven, twelve, thirteen, fourteen, fifteen, sixteen, seventeen, eighteen, nineteen, or twenty beads (or first partitions). In some cases, the resulting droplets (or second partitions) may each comprise, on average, at least about one, two, three, four, five, six, seven, eight, nine, ten, eleven, twelve, thirteen, fourteen, fifteen, sixteen, seventeen, eighteen, nineteen, twenty, or more beads (or first partitions).

The methods, compositions, and devices of the present disclosure may be used with many suitable oils. In some cases, an oil may be used to generate an emulsion. The oil may comprise fluorinated oil, silicon oil, mineral oil, vegetable oil, and combinations thereof.

The template oligonucleotide (e.g., containing barcode) sequences can be attached to the beads within the partition by a reaction such as a primer extension reaction, ligation reaction, or other methods. For example, in some cases, beads functionalized with primers can be combined with template barcode oligonucleotides that comprise a binding site for the primer, enabling the primer to be extended on the bead. After multiple rounds of amplification, copies of the single barcode sequence can be attached to the multiple primers attached to the bead. After attachment of the barcode sequences to the beads, the emulsion can be broken and the barcoded beads (or beads linked to another type of amplified product) can be separated from beads without amplified barcodes. Additional sequences, such as a random sequence (e.g., a random N-mer) or a nucleic acid target sequence, can then be added to the bead-bound barcode sequences, using, for example, primer extension methods or other amplification reactions. This process can generate a large and diverse set of barcoded beads.

Barcodes can be generated from a variety of different formats, including bulk synthesized polynucleotide barcodes, randomly synthesized barcode sequences, microarray based barcode synthesis, native nucleotides, partial complement with N-mer, random N-mer, pseudo random N-mer, or combinations thereof. Synthesis of barcodes is described herein, as well as in, for example, in U.S. Patent Publication No. 2014/0228255, the full disclosure of which is incorporated herein by reference in its entirety for all purposes.

The barcodes may be loaded into beads so that one or more barcodes are introduced into a particular bead. In some cases, each bead may contain the same set of barcodes. In some cases, each bead may contain different sets of barcodes. In some cases, each bead may comprise a set of identical barcodes. In some cases, each bead may comprise a set of different barcodes.

Template oligonucleotide can incorporate additional sequence segments other than barcode sequence segments. Such additional sequence segments can include functional sequences, such as primer sequences, and primer annealing site sequences. In addition, functional sequences can include, for example, immobilization sequences for immobilizing barcode containing sequences onto surfaces, e.g., for sequencing applications. For ease of discussion, a number of specific functional sequences are described below, such as primers of P5, P7, Read1primer, and Read2primer (or others), sample indexes, random N-mers, etc., and partial sequences for these, as well as complements of any of the foregoing. However, it will be appreciated that these descriptions are for purposes of discussion, and any of the various functional sequences included within the barcode containing oligonucleotides can be substituted for these specific sequences, including without limitation, different attachment sequences, different sequencing primer regions, different N-mer regions (targeted and random), as well as sequences having different functions, e.g., secondary structure forming, e.g., hairpins or other structures, probe sequences, e.g., to allow interrogation of the presence or absence of the oligonucleotides or to allow pull down of resulting amplicons, or any of a variety of other functional sequences.

Also included within this disclosure are methods of sample preparation for nucleic acid analysis, and particularly for sequencing applications. Sample preparation can generally include, e.g., obtaining a sample comprising sample nucleic acid from a source, optionally further processing the sample, combining the sample nucleic acid with barcoded beads, and forming emulsions containing fluidic droplets comprising the sample nucleic acid and the barcoded beads. Droplets can be generated, for example, with the aid of a microfluidic device and/or via any suitable emulsification method. The fluidic droplets can also comprise agents capable of dissolving, degrading, or otherwise disrupting the barcoded beads, and/or disrupting the linkage to attached sequences, thereby releasing the attached barcode sequences from the bead. The barcode sequences can be released either by degrading the bead, detaching the oligonucleotides from the bead such as by a cleavage reaction, or a combination of both.

By amplifying (e.g., via amplification methods described herein) the sample nucleic acid in the fluidic droplets, the free barcode sequences can be attached to the sample nucleic acid. The emulsion comprising the fluidic droplets can then be broken and, if desired, additional sequences (e.g., sequences that aid in particular sequencing methods, additional barcode sequences, etc.) can then be added to the barcoded sample nucleic acid using, for example, additional amplification methods. Sequencing can then be performed on the barcoded, amplified sample nucleic acid and one or more sequencing algorithms applied to interpret the sequencing data. As used herein, the sample nucleic acids can include any of a wide variety of nucleic acids, including, e.g., DNA and RNA, and specifically including for example, genomic DNA, cDNA, mRNA total RNA, and cDNA created from mRNA or total RNA transcript.

The methods and compositions of this disclosure can be used with any suitable digital processor. The digital processor can be programmed, for example, to operate any component of a device and/or execute methods described herein. In some cases, bead formation can be executed with the aid of a digital processor in communication with a droplet generator. The digital processor can control the speed at which droplets are formed or control the total number of droplets that are generated. In some cases, attaching barcode sequences to sample nucleic acid can be completed with the aid of a microfluidic device and a digital processor in communication with the microfluidic device. In some cases, the digital processor can control the amount of sample and/or beads provided to the channels of the microfluidic device, the flow rates of materials within the channels, and the rate at which droplets comprising barcode sequences and sample nucleic acid are generated.

The methods and compositions of this disclosure can be useful for a variety of different molecular biology applications including, but not limited to, nucleic acid sequencing, protein sequencing, nucleic acid quantification, sequencing optimization, detecting gene expression, quantifying gene expression, epigenetic applications, and single-cell analysis of genomic or expressed markers. Moreover, the methods and compositions of this disclosure can have numerous medical applications including identification, detection, diagnosis, treatment, staging of, or risk prediction of various genetic and non-genetic diseases and disorders including cancer.

Barcoding Sample Materials and/or Fragments Thereof

The methods, compositions and systems described herein may be useful for attaching barcodes, and particularly barcode nucleic acid sequences, to sample materials and/or components/fragments thereof. In general, this can be accomplished by partitioning sample material components/fragment into separate partitions or reaction volumes in which are co-partitioned a plurality of barcodes, which are then attached to sample components/fragment within the same partition. Methods to attach barcodes to sample components/fragments thereof may include ligation method, chain extension method, and transposase method.

In an example process, a first partition can be provided that can include a plurality of first oligonucleotides (e.g., nucleic acid barcode molecules) that each can comprise a common nucleic acid barcode sequence. The first partition can comprise any of a variety of portable partitions, e.g., a bead (e.g., a degradable bead, a gel bead), a droplet (e.g., an aqueous droplet in an emulsion), a microcapsule, or the like, to which the first oligonucleotides are releasably attached, releasably coupled, or are releasably associated. Moreover, any suitable number of first oligonucleotides can be included in the first partition. For example, the first oligonucleotides can be releasably attached to, releasably coupled to, or releasably associated with the first partition via a cleavable linkage such as, for example, a chemically cleavable linkage (e.g., a disulfide linkage, or any other type of chemically cleavable linkage), a photocleavable linkage, and/or a thermally cleavable linkage. In some cases, the first partition can be a bead and the bead can be a degradable bead (e.g., a photodegradable bead, a chemically degradable bead, a thermally degradable bead, or any other type of degradable bead). Moreover, the bead can comprise chemically-cleavable cross-linking (e.g., disulfide cross-linking).

The first partition can then be co-partitioned into a second partition, together with a sample material, sample material component, fragment of a sample material, or a fragment of a sample material component. The sample material (or component or fragment thereof) can be any appropriate sample type. In cases where a sample material or component of a sample material comprises one or more nucleic acid fragments, the one or more nucleic acid fragments can be of any suitable length. The second partition can include any of a variety of partitions, including for example, wells, microwells, nanowells, tubes or containers, or in some cases droplets (e.g., aqueous droplets in an emulsion) or microcapsules in which the first partition can be co-partitioned. In some cases, the first partition can be provided in a first aqueous fluid and the sample material, sample material component, or fragment of a sample material component can be provided in a second aqueous fluid. During co-partitioning, the first aqueous fluid and second aqueous fluid can be combined within a droplet within an immiscible fluid. In some cases, the second partition can comprise no more than one first partition. In some cases, the second partition can comprise no more than one, two, three, four, five, six, seven, eight, nine, or ten first partitions. In some cases, the second partition can comprise at least one, two, three, four, five, six, seven, eight, nine, ten, or more first partitions.

Once co-partitioned, the first oligonucleotides comprising the barcode sequences can be released from the first partition (e.g., via degradation of the first partition, cleaving a chemical linkage between the first oligonucleotides and the first partition, or any other suitable type of release) into the second partition, and attached to the sample components co-partitioned therewith. In some cases, the first partition can comprise a bead and the crosslinking of the bead can comprise a disulfide linkage. In addition, or as an alternative, the first oligonucleotides can be linked to the bead via a disulfide linkage. In either case, the first oligonucleotides can be released from the first partition by exposing the first partition to a reducing agent (e.g., dithiothreitol (DTT) or tris(2-carboxyethyl)phosphine (TCEP)).

Attachment of the barcodes to sample components can include the direct attachment of the barcode oligonucleotides to sample materials, e.g., through ligation, hybridization, or other associations. Additionally, in many cases, for example, in barcoding of nucleic acid sample materials (e.g., template nucleic acid sequences, template nucleic acid molecules), components or fragments thereof, such attachment can additionally comprise the use of the barcode-containing oligonucleotides as priming sequences. The priming sequence can be complementary to at least a portion of a nucleic acid sample material and can be extended along the nucleic acid sample materials to create complements to such sample materials, as well as at least partial amplification products of those sequences or their complements.

In another example process, a plurality of first partitions can be provided that comprise a plurality of different nucleic acid barcode sequences. Each of the first partitions can comprise a plurality of nucleic acid barcode molecules having the same nucleic acid barcode sequence associated therewith. Any suitable number of nucleic acid barcode molecules can be associated with each of the first partitions, including, for example, at least about 2, 10, 100, 500, 1000, 5000, 10000, 50000, 100000, 500000, 1000000, 5000000, 10000000, 50000000, or 1000000000, or more than 1000000000 different nucleic acid barcode sequences.

As discussed above, the first partitions can be co-partitioned with sample materials, fragments of a sample material, components of a sample material, or fragments of a component(s) of a sample material into a plurality of second partitions. In some cases, a subset of the second partitions can comprise the same nucleic acid barcode sequence. For example, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more than 95% of the second partitions can comprise the same nucleic acid barcode sequence. Moreover, the distribution of first partitions per second partition can also vary according to, for example, occupancy rates described elsewhere herein. In cases where the plurality of first partitions comprises a plurality of different first partitions, each different first partition can be disposed within a separate second partition.

Following co-partitioning, the nucleic acid barcode molecules associated with the first partitions can be released into the plurality of second partitions. The released nucleic acid barcode molecules can then be attached to the sample materials, sample material components, fragments of a sample material, or fragments of sample material components, within the second partitions. In the case of barcoded nucleic acid species (e.g., barcoded sample nucleic acid, barcoded template nucleic acid, barcoded fragments of one or more template nucleic acid sequences, etc.), the barcoded nucleic acid species can be sequenced.

In another example process, an activatable nucleic acid barcode sequence can be provided and partitioned with one or more sample materials, components of a sample material, fragments of a sample material, or fragments of a component(s) of a sample material into a first partition. With the first partition, the activatable nucleic acid barcode sequence can be activated to produce an active nucleic acid barcode sequence. The active nucleic acid barcode sequence can then be attached to the one or more sample materials, components of a sample material, fragments of a sample material, or fragments of a component(s) of a sample material.

In some cases, the activatable nucleic acid barcode sequence can be coupled to a second partition that is also partitioned in the first partition with the activatable nucleic acid barcode sequence. An activatable nucleic acid barcode sequence can be activated by releasing the activatable nucleic acid barcode sequence from an associated partition (e.g., a bead). Thus, in cases where an activatable nucleic acid barcode sequence is associated with a second partition (e.g., a bead) that is partitioned in a first partition (e.g., a fluidic droplet), the activatable nucleic acid barcode sequence can be activated by releasing the activatable nucleic acid barcode sequence from its associated second partition. In addition, or as an alternative, an activatable barcode can also be activated by removing a removable blocking or protecting group from the activatable nucleic acid barcode sequence.

In another example process, a sample of nucleic acids can be combined with a set of barcoded beads (including types of beads described elsewhere herein) to form a mixture. In some cases, the barcodes of the beads may, in addition to a barcode sequence, each comprise one or more additional sequences such as, for example, a universal sequence and/or a functional sequence (e.g., a random N-mer or a targeted N-mer). The mixture can be partitioned into a plurality of partitions, with at least a subset of the partitions comprising at most one barcoded bead. Within the partitions, the barcodes can be released from the beads, using any suitable route, including types of release described herein. A set of barcoded beads can be generated via any suitable route, including the use of methods and compositions described elsewhere herein. In some cases, the sample of nucleic acids can be combined with the set of barcoded beads and/or the resulting mixture partitioned with the aid of a microfluidic device. In cases where the released barcodes also comprise a primer sequence (e.g., such as a targeted N-mer or a random N-mer as described elsewhere herein), the primer sequences of the barcodes can be hybridize with the sample nucleic acids and, if desired, an amplification reaction can be completed in the partitions.

The beads provided herein can be attached to oligonucleotide sequences that are random, pseudo-random, or targeted N-mers capable of priming a sample (e.g., genomic sample) in a downstream process. In some cases, the same N-mer sequences may be present on the oligonucleotides attached to a single bead or bead population. This may be the case for targeted priming methods, e.g., where primers are selected to target certain sequence segments within a larger target sequence. In some cases, each bead within a population of beads herein can be attached to a large and diverse number of N-mer sequences to diversify the sampling of these primers against template molecules, as such random N-mer sequences will randomly prime against different portions of the sample nucleic acids.

The length of an N-mer can vary. In some cases, an N-mer (e.g., a random N-mer, a pseudo-random N-mer, or a targeted N-mer) may be between about 2 and about 100 nucleotides in length, between about 2 and about 50 nucleotides in length, between about 2 and about 20 nucleotides in length, between about 5 and about 25 nucleotides in length, or between about 5 and about 15 nucleotides in length. In some cases, an N-mer (e.g., a random N-mer, a pseudo-random N-mer, or a targeted N-mer) may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, an N-mer (e.g., a random N-mer, a pseudo-random N-mer, or targeted a N-mer) may be greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some cases, an N-mer (e.g., a random N-mer, a pseudo-random N-mer, or a targeted N-mer) may be less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

Process of Barcoding Fragments Using a Ligation Process in a Partition

The present disclosure provides methods, and systems for preparing improved sets of sequencing samples from sample nucleic acids. The improved set of sequencing samples provide more uniform coverage, lower sequence error rates, higher amplification rates of the original sequence, and lower chimera generation rates when constructing the set of sequencing samples.

In cases, sets of barcoded samples can be prepared through the ligation of the barcode oligonucleotides to the partitioned nucleic acids. Generally speaking, a set fragments can be created within a partition from initially long nucleic acid contained within that partition, in order to preserve the molecular context of the long nucleic acid. The set of fragments can be prepared in a fashion that leaves the fragments of the long nucleic acid available for ligation with the barcoded oligonucleotides co-partitioned with those fragments, e.g., via a bead based delivery system as described herein.

Figure 2:
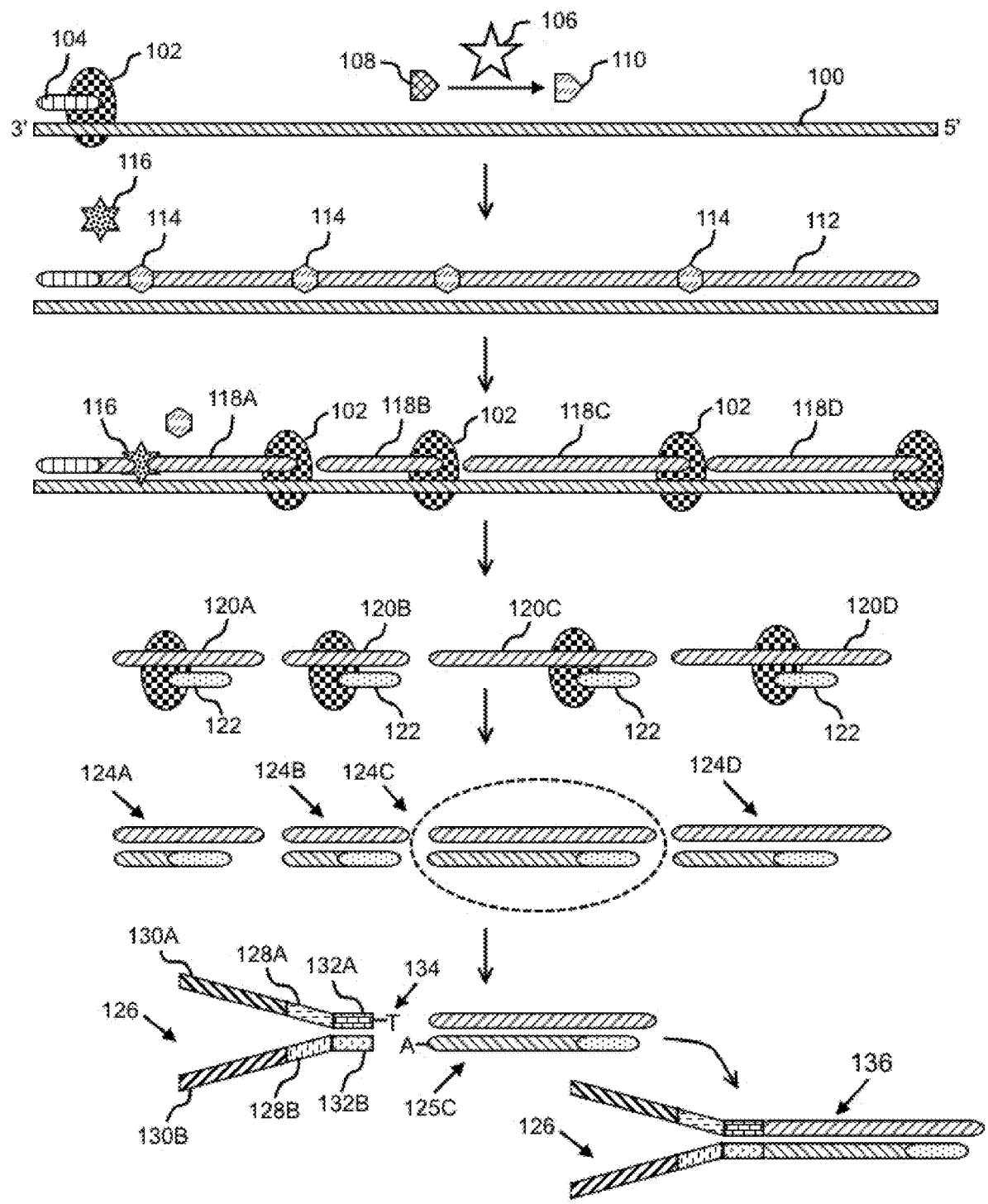
FIG. 2 is a diagram depicting a barcoding process utilizing ligation processes on amplified fragments.

One example process is illustrated in FIG. 2, which depicts that a single-stranded sample nucleic acid 100, for example, a sample nucleic acid partitioned into a droplet or other partition, can be fragmented into shorter fragments within the partition, allowing the fragments to be ligated with barcoded oligonucleotides. As illustrated, the fragmenting operation can be carried out by first replicating the single-stranded sample nucleic acid 100 using a high fidelity polymerase 102, e.g., a phi29 DNA polymerase. The replicating operation may be carried out by a random priming and extension process, e.g., using a first random N-mer primer 104, e.g., hexamer, 7-mer, 8-mer, 9-mer, 10-mer or larger. The first random N-mer primer 104 can be used to generate random fragments from the single-stranded sample nucleic acid 100 by (1) annealing to random locations on the single-stranded sample nucleic acid 100 and (2) being extended by the polymerase 102, e.g., phi29 DNA polymerase, or the like in the presence of dNTPs. Multiple N-mer primers 104 can anneal to the same nucleic acid template to introduce multiple initiation site for multiple polymerase 102 to extend the N-mer primers.

Alternatively, the replicating operation can prime off of a known terminal sequence segment that may be provided as an adapter sequence ligated to the double-stranded sample nucleic acid comprising the single-strand sample nucleic acid 100, e.g., during a pre-partitioning sample preparation step. The adapter sequences can provide a known nicking site within each strand of the sample nucleic acid and in the presence of an appropriate nicking enzyme, a DNA polymerase capable of priming off of the nicked strand, e.g., phi29 polymerase, may be used to replicate one strand while displacing the other strand. Multiple nicking sites may be present in the same double-stranded sample nucleic acid.

In addition, a dCTP generating enzyme 106 can convert an enzyme substrate 108 into reagent dUTP 110 during the replication process. An example of such a reaction can be a dCTP deaminase-catalyzed conversion of dCTP into dUTP 110. The reagent dUTP 110, in turn, can be processed by the DNA polymerase 102 in the replication process with other dNTPs. In some cases, the replication can be carried out with a low level concentration of dUTP at the beginning stage of the amplification, in order to create a copied strand 112 with uracil-containing bases 114 randomly dispersed throughout the copied strand 112. In some cases, a high level concentration of dUTP can be provided near the end of the amplification process, in order to generate shorter fragments, as described herein.

Subsequently, a uracil excising enzyme 116 in the partition can generate a single nucleotide gap within the copied strand 112 at the location of the incorporated uracil-containing bases 114, but creates no such gap in the single-strand sample nucleic acid 100. An example of the uracil excising enzyme 116 can be uracil DNA glycosylase (UDG), e.g., as found in the Uracil Specific Excision Reagent, or USER (available from New England Biolabs). Consequently, the copied strand 112 can be fragmented into fragments 118A, 118B, 118C, and 118D, as shown in FIG. 2.

Other fragments can be generated by allowing the polymerase 102 to extend these fragments 118A-118D, starting from the 3' ends of the nicking sites, both displacing the adjacent first set of fragments, e.g., 118A-118D, and creating further replicate copies of the single-strand sample nucleic acid 100, wherein these new replicate copies incorporate uracil-containing bases 114 at randomly dispersed intervals. These new replicate copies can then be fragmented as shown above due to the incorporation of uracil-containing bases. One advantage of using the random nicking sites for the polymerase 102 to replicate the single-stranded sample nucleic acid 100 can be to reduce priming bias that may come from exogenously introduced sequence-specific primers. The method in the present disclosure can allow the creation of a less biased set of fragments from the original sample nucleic acid.

At some point, amplified fragments 120A, 120B, 120C, and 120D, which are replicate copies, can be released from the single-stranded sample nucleic acid 100. Once these fragments are generated, they may be further replicated using, e.g., a second random N-mer primers 122, which has been co-partitioned with the fragments 120A-120D. The replication of these fragments 120A-120D using the second random N-mer primer 122 can result in the creation of double stranded, blunt-ended fragments 124A-124D of varying lengths.

Once the blunt-ended fragments 124A-124D are created, they may be processed in order to attach double stranded barcode oligonucleotides that are co-partitioned with the fragments 124A-124D, e.g., via the bead based delivery systems described herein. For example, as shown in FIG. 2, the blunt-ended fragment 124C can be first A-tailed at its 3'-end, using, e.g., Taq polymerase or Klenow polymerase, to give A-tailed fragment 125C. The A-tailed fragment 125C can then be ligated to the double stranded dual-index adaptor 126. The adaptor 126 can include barcode segments 128A and 128B, as well as functional sequences, such as P5 segment 130A, P7 segment 130B, Read1primer segment 132A, and Read2primer segment 132B, along with the complementary T-base overhang 134 on the 3'-end of the adaptor 126 at the ligation point. A standard ligation enzyme system, e.g., a T4 ligase, can be used to ligate the A-tailed fragment 125C with the adaptor 126. As a result, a barcoded, double stranded fragment 136 can be created. Fragment 136 can include the adaptor 126. The barcoded fragment 136 may then be subjected to one or more additional processing operations, e.g., to be amplified; to attach adapter sequences at the opposite end of the adaptor 126, or to be processed by a nuclease to afford an optimal sized fragment.

In some cases, other methods to attach a barcode to a nucleic acid fragment can include a nucleic acid extension enzyme and a transposase. In some cases, the set of amplified nucleic acid sequences can include a single stranded DNA and the ligating enzyme can include an ATP independent enzyme. The ATP independent enzyme can include thermostable 5' AppDNA/RNA ligase, which is an ATP independent RNA ligase from *Methanobacterium* thermoautotrophicum (Mth RNA ligase). This enzyme may ligate a 5' pre-adenylated linker to the 3'-OH end of either RNA or single-stranded DNA. In some cases, the ligating enzyme may include a topoisomerase. The topoisomerase can be topoisomerase I. In some cases, the ligating enzyme can include T4 DNA ligase.

CRISPR-Cas Complex

Recent advances in genome-editing technologies led to the discovery of the clustered regularly interspaced short palindromic repeat (CRISPR) arrays and their CRISPR associated (Cas) proteins. See, Wiedenheft, B., "RNA-guided genetic silencing systems in bacteria and archaea," *Nature* (2012) 482(7385):331-8, which is entirely incorporated herein by reference. CRISPRs are DNA loci comprising short repetitions of base sequences that function as an immune system in bacteria, providing acquired immunity against invading foreign DNA via RNA-guided cleavage. When paired with a Cas nuclease, such as, for example, a Cas9 nuclease, which is an RNA-guided DNA endonuclease from a type II CRISPR system, CRISPRs can lead to the cleavage of genomic DNA in a site-specific manner. Thus, a CRISPR-Cas nuclease system is a protein-RNA complex that uses an RNA molecule as a guide to localize the complex to a target DNA sequence via base-pairing.

The defense activity of a CRISPR-Cas system generally includes three stages: (1) adaptation, wherein a Cas protein complex excises a fragment of the target DNA and inserts it into the CRISPR array as a spacer; (2) expression and processing of the precursor CRISPR (pre-cr) RNA resulting in the formation of mature crRNAs; and (3) interference, wherein the effector module (either another Cas protein complex or a single large protein) is guided by a crRNA to recognize and cleave target DNA/RNA. The adaptation stage can be mediated by the complex of the Cas1 and Cas2 proteins, or involving additional Cas proteins. See, Barrangou, R., and Marraffini, L. A. "CRISPR-Cas systems: Prokaryotes upgrade to adaptive immunity," *Mol. Cell* (2014) 54(2): 234-244, which is entirely incorporated herein by reference.

One way to classify CRISPR-Cas systems can be based on the configuration of their effector modules: class 1 CRISPR-Cas systems employ several Cas proteins and the crRNA to form an effector complex, whereas class 2 CRISPR-Cas systems utilize a large single-component Cas protein in conjunction with crRNAs to mediate interference. Makarova, K. S., and Koonin, E. V. "Annotation and classification of CRISPR-Cas systems," *Methods Mol. Biol.* (2015) 1311, 47-75, which is entirely incorporated herein by reference.

One type of class 2 CRISPR-Cas protein is called CRISPR-Cas9, which is type II and employs homologous RNA-guided endonucleases as effectors. Another type of class 2 CRISPR-Cas protein is tentatively assigned type V, which contains a large, about 1,200-1,300 amino acid protein called Cpf1. Report shows that Cpf1 enzyme from *Francisella novicida, Acidaminococcus* sp. BV3L6, and *Lachnospiraceae* bacterium ND2006 encode functional defense systems capable of mediating interference in bacterial cells guides by the CRISPR spacers. Zetsche, B. et al. "Cpf1 Is a Single RNA-Guided Endonuclease of a Class 2 CRISPR-Cas System," *Cell* (2015) 163(3):759-71, which is entirely incorporated herein by reference. Cpf1 may differ from Cas9 in at least three aspects: (1) Cpf1-associated CRISPR arrays are processed into mature crRNAs without the requirement of trans-activating crRNA (tracrRNA); (2) Cpf1-crRNA complex cleave target DNA, which is proceeded by a thymidine-rich protospacer-adjacent motif (PAM), while Cas9 recognize a guanidine-rich PAM following the target DNA to be cleaved; and (3) Cpf1 introduces a staggered DNA double-strand break with a 4- and 5-nucleotide 5' overhang, in contrast to the blunt ends generated by Cas9. Zetsche, B. et al., *Cell* (2015) 163(3): 759-71. In addition, although both Cpf1 and Cas9 make double-strand breaks, Cpf1 uses a RuvC-like domain to cut while Cas9 uses its RuvC- and HNH-like domains to make the cut. There are other class 2 CRISPR-Cas systems, including, for example, type IIA Csn2 protein (e.g., from *S. thermophiles* and *S. pyogenes*), type IIB Cas4 protein, type IIC CRISPR-Cas protein (e.g., from *N. meningitidis*) requires three genes cas1, cas2 and cas9, type V C2c1 and C2c3 proteins, and type VI C2c2 protein (also called Cas13a).

Based on the type II CRISPR-Cas9 mechanism, researchers created a single guide RNA (sgRNA), a chimeric form of naturally occurring CRISPR RNA (crRNA) and transactivating crRNA (tracrRNA). The binding of sgRNA to a specific double stranded DNA sequence resulted in double strand breaks at the target site on the hybridized DNA. See, Cong, L., "Multiplex genome engineering using CRISPR/Cas systems," *Science* (2013) 339 (6121):819-23; Mali, P., "RNA-guided genome engineering via Cas9," *Science* (2013) 339 (6121):823-6, both of which are entirely incorporated herein by reference. When co-expressed with a sgRNA, a catalytically inactive Cas protein, for example, a catalytically inactive Cas9 which lacks endonuclease activity, generates a DNA recognition complex that can specifically interfere with transcriptional elongation, RNA polymerase binding, or transcription factor binding. See, Qi, L. S., "Repurposing CRISPR as an RNA-Guided Platform for Sequence-Specific Control of Gene Expression," *Cell* (2013) 152(5):1173-83, which is entirely incorporated herein by reference.

Thus, CRISPR-Cas system can be modified to perform functions other than genome editing. For example, the binding preference of Cas proteins for DNA sequence can be changed by varying the sgRNA sequence to complement the target DNA sequence for recognition. When the desired sgRNA sequence is co-expressed with Cas protein, the Cas protein can recognize the desired target DNA sequence instead of the original DNA sequence for the wild type Cas protein. For example, the *S. pyogenes* CRISPR system can be introduced into the *E. coli* system by expressing the Cas9 protein from an anhydrotetracycline (aTc)-inducible promoter on a plasmid containing a p15A replication origin. Meanwhile, the sgRNA can be expressed from a minimal constitutive promoter on a plasmid containing a ColE1 replication origin. Confirmation of a successful Cas9 protein thus obtained can be tested by assessing the nuclease activity of the expressed Cas9 protein for the target DNA nuclease (complementary to sgRNA). In some cases, the sgRNA molecules co-expressed with Cas9 protein can contain an about 20 nucleotide (nt) target specific complementary region, an about 42 nt Cas9-binidng hairpin (also known as Cas9 handle), and an about 40 nt transcription terminator derived from *S. pyogenes*. In some cases, the sgRNA molecules can contain from about 17 to about 24 nt target specific complementary region. In some cases, the sgRNA molecules can contain a Cas protein-binding hairpin with the length of from about 35 to about 50 nt.

Once the expression of the desired Cas protein, such as, for example, a Cas9 protein, in *E. coli* has been confirmed, its endonuclease activity of the Cas protein can be reduced or eliminated by mutations of amino acids critical to the endonuclease activity of the Cas protein. For example, two silencing mutations of the RuvC1 and HNH nuclease domains (D10A and H841/A) of Cas9 proteins can be utilized to create catalytically inactive Cas9 proteins devoid of nuclease cleaving activities. Other mutations, deletions, or insertion to knock out the endonuclease activity of the Cas proteins are possible.

In some cases, mutation can be accomplished using mutagenesis on plasmid containing wild type Cas protein DNA fragment, such as, for example, Cas9 DNA fragment in plasmid 46168 from Addgene (Cambridge, MA), using commercial kits, such as, for example, Site-Directed Mutagenesis Plus System (ThermoFisher Scientific, (Waltham, MA). See, Friedland A. E., et al. "Heritable genome editing in *C. elegans* via a CRISPR-Cas9 system," *Nat. Methods* (2013) 10(8):741-3, which is entirely incorporated herein by reference. The mutated dCas9 DNA can then be cloned into vectors, such as, for example, AgeI and NheI restricted L4440 vector. DNA domains coding for the spacer peptide linker and the linked endonuclease can be ligated into the previously obtained dCas9/L4440 plasmid to generate constructs. Further molecular cloning operations, such as, for example, incorporation of nuclear localization signals (NLSs) sequence, may be performed to make the final cassettes for the dCas9 system of the present disclosure. The resulting dCas9 cassettes can be cloned into another plasmid, such as pPD95_75 at its XmaI and EcoRI sites. Specific promoters can be placed upstream of the dCas9 cassette in pPD95_75. Further operations can be formed to express and purify proteins, including CRISPR-Cas proteins, based on the dCas9 cassette obtained above.

Target-specific single guided RNA (sgRNA) can be synthesized according to the Cas protein used for the CRISPR-Cas system of the present disclosure. For example, for Cas9 proteins, the sequence requirements for sgRNA can be: (1) a protospacer adjacent motif (PAM) sequence, such as, NGG, can be placed at the 3' end of the target sequence; and (2) the first nucleotide at 5' end of the target sequence can be set to G, thereby allowing efficient sgRNA transcription mediated by the U6 promoter in vivo or T7 promoter in vitro.

As discussed above, both the limitations of the NGS sequencing instrumentation and the specific sequencing application employed determine the optimal DNA insert size for the final set of fragments for sequencing. Regarding the influence of sequencing instrumentation, Illumina sequencers rely on the process of cluster generation for the samples for analysis to be distributed and amplified on the surface of flow-cells. When using an Illumina sequencer, members of the samples for analysis with shorter DNA insert may amplify more efficiently and allow greater data density than members of the samples for analysis with longer DNA insert. But longer DNA inserts may generate larger, more diffuse clusters than shorter DNA inserts. Other factors impacting optimal fragment size in a set of sequencing samples include read mapability (longer fragment size can be better), enrichment resolution and specificity (shorter fragment size can be better), reading errors accumulation (shorter fragment size can be better). Therefore, an optimal range of DNA inserts can be desirable for better sequencing efficiency/quality. For Illumina sequencers, the optimal fragment size for a single-end (SE) sequencing can be from 150 to 300 base pair (bp), while the optimal fragment size for a paired-end (PE) sequencing can be from 250 to 500 bp. These optimal fragment sizes give tighter peaks for the sequencing reads and are long enough to be mapped uniquely to deduce the sequence of the target nucleic acid.

The present disclosure provides methods, systems and compositions to control the size range of sequencing sample fragments within a defined size range. The improved control over the size range of sample fragments can be adjusted according to the types of sequencing technology used for the set of sequencing samples according to the optimal range of fragment sizes for the particular sequencing technology.

In some cases, a first set of barcoded fragments with varying fragment sizes for DNA inserts can be processed by a CRISPR-Cas complex, e.g., a CRISPR-Cas targeted endonuclease system, to produce a second set of barcoded fragments with a more defined range of fragment sizes for DNA inserts. As used herein, a defined range generally refers to a tighter distribution of fragment sizes for DNA inserts. For example, when compared with the starting DNA fragments, a defined range for the product DNA fragments may generally refer to a higher percentage of the product DNA fragments distributing within the same desired range of fragment sizes or the same percentage of the product DNA fragments distributing within a narrower range of desired fragment sizes.

Figure 3:
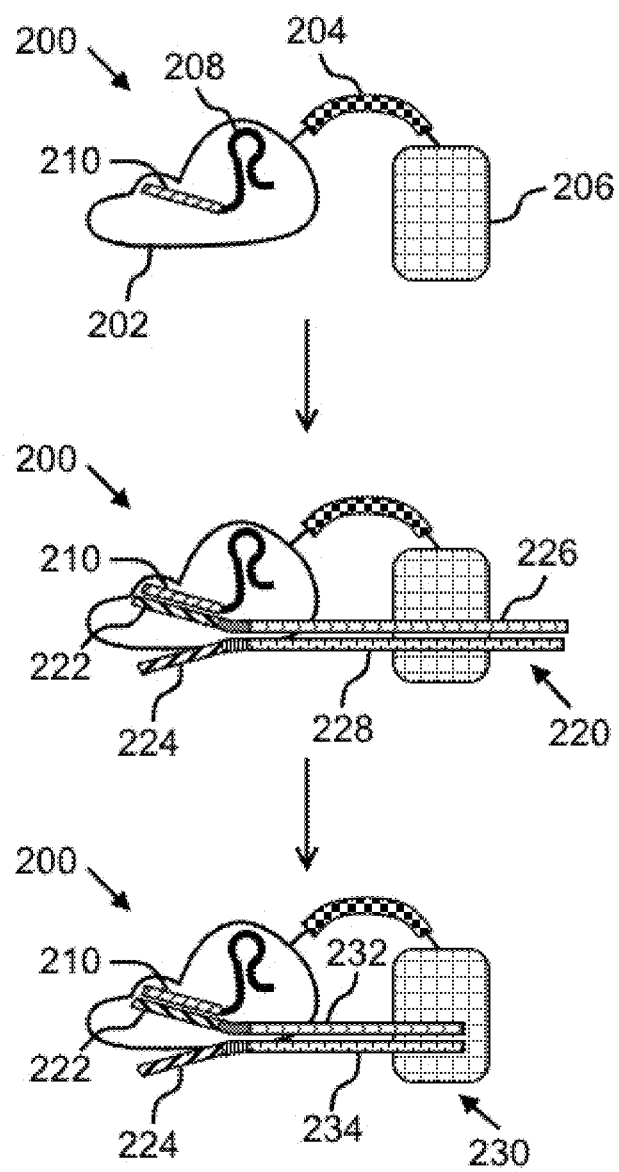
FIG. 3 shows an example clustered regularly interspaced short palindromic repeat (CRISPR)-CRISPR associated protein (Cas) complex and an example mechanism of action of the CRISPR-Cas complex.

Referring now to the drawings, and with specific reference to FIG. 3, there is depicted an example CRISPR-Cas targeted endonuclease system 200 wherein various embodiments of the present disclosure can be utilized. In this example, the CRISPR-Cas targeted endonuclease system 200 comprises a catalytically inactive Cas nuclease, such as, for example, a catalytically inactive Cas9 protein 202, a spacer peptide 204, an endonuclease 206, and a single guide RNA (sgRNA) 208.

Catalytically inactive Cas9 protein 202 may generally and interchangeably be referred to as a "dCas9" protein. Methods for generating a dCas9 protein (or a fragment thereof) may include those disclosed (See, e.g., Jinek, M., "A programmable dual-RNA-guided DNA endonuclease in adaptive bacterial immunity" *Science* (2012) 337(6096):816-21; Qi, L. S., "Repurposing CRISPR as an RNA-Guided Platform for Sequence-Specific Control of Gene Expression," *Cell* (2013) 152(5):1173-83, both of which are entirely incorporated herein by reference). The DNA cleavage domain of Cas9 is disclosed to include two subdomains, the HNH nuclease subdomain and the RuvC1 subdomain. The HNH subdomain cleaves the DNA strand complementary to the guide RNA, whereas the RuvC1 subdomain cleaves the non-complementary DNA strand. Mutations within the HNH nuclease and RuvC1 subdomains can deactivate the nuclease functionality of Cas9. For example, the mutations D10A and H841A completely inactivate the nuclease activity of Cas9 from *S. pyogenes* (Jinek, M., *Science* (2012) 337(6096):816-21; Qi, L. S., *Cell*. (2013) 152(5):1173-83).

Wild type Cas nuclease can be deactivated by a mutation (e.g., substitution, insertion, deletion) of one or more amino acids (e.g., 2 or more amino acids, 3 or more amino acids, 4 or more amino acids, 5 or more amino acids, etc.) (e.g., relative to a wild type Cas nuclease) to produce a variant Cas nuclease. Such mutations can cause a reduction of the nuclease cleavage activity (cleavage of the double stranded target nucleic acid) of the variant Cas nuclease relative to the nuclease cleavage activity of a corresponding wild type Cas nuclease. In some cases, the variant Cas nuclease can have a nuclease cleavage activity that is 90% or less of the nuclease cleavage activity of a corresponding wild type Cas nuclease (e.g., 85% or less, 80% or less, 70% or less, 60% or less, 50% or less, 40% or less, 30% or less, 20% or less, 15% or less, 10% or less, or 5% or less of the nuclease cleavage activity of a corresponding wild type Cas nuclease). In some cases, a variant Cas nuclease can have substantially no nuclease cleavage activity compared to the nuclease cleavage activity of a corresponding wild type Cas nuclease.

In some cases, Cas9 proteins comprising fragments of Cas9 can be provided. In some cases, proteins comprising Cas9 or fragments thereof are generally referred to as "Cas9 variants." A Cas9 variant shares homology to dCas9, or a fragment thereof. For example a Cas9 variant can be at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some cases, the Cas9 variant can comprise a fragment of Cas9, such that the fragment can be at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding fragment of wild type Cas9. In some cases, Cas9 variants may include dCas9 proteins, and/or variants of dCas9 proteins.

In some cases, dCas9 variants which have mutations other than or in addition to mutations of D10A and H820A can be provided. Such mutations, by way of example, can include other amino acid substitutions at D10 and H820, or other substitutions within the nuclease domains of Cas9 (e.g., substitutions in the HNH nuclease subdomain and/or the RuvC1 subdomain). In some cases, variants or homologues of dCas9 can be provided which may be at least about 70% identical, at least about 80% identical, at least about 90% identical, at least about 95% identical, at least about 98% identical, at least about 99% identical, at least about 99.5% identical, or at least about 99.9% to the dCas9 with only mutations of D10A and H820A. In some cases, variants of dCas9 can be provided having amino acid sequences which are shorter, or longer than the dCas9 with only mutations of D10A and H820A, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some cases, Cas9 protein generally refers to Cas9 proteins obtained from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

Spacer peptide 204 refers to a peptide or protein molecule linking dCas9 protein 202 and endonuclease 206. Typically, the spacer peptide 204 can be positioned between, or flanked by, dCas9 protein 202 and endonuclease 206, and connected to dCas9 protein 202 and endonuclease 206 via covalent bonds, thus connecting the two. In some cases, the spacer peptide can be an amino acid or a plurality of amino acids (e.g., a peptide or protein). In some cases, the spacer peptide is 5-700 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, 150-200, 200-250, 250-300, 300-350, 350-400, 400-450, 450-500, 500-550, 550-600, 600-650, and 650-700 amino acids in length. Longer or shorter spacer peptides can also be possible. In some cases, the spacer peptide can comprise an alpha-helical peptide. In some cases, the spacer peptide can be an unstructured peptide. In some cases, the spacer peptide can comprise unnatural amino acid or organic molecules other than an amino acid. In some cases, the spacer peptide can comprise an intramolecular bond between two amino acid moieties, such as, for example, a disulfide bond, or a substituted or unsubstituted cross-linker comprising an alkanediyl group and/or an alkenediyl group. In some cases, the spacer peptide can comprise positively charged groups, such as, for example, a primary amine group, a guanidine group, and an imidazole group. In some cases, the spacer peptide can interact with double-stranded DNA due to its positively charged groups which attract negatively charged phosphate groups on the DNA.

In some cases, spacer peptide 204 can comprise an alpha helix-forming linker. In some cases, an alpha helix forming linker can comprise $(EAAAK)_n$, wherein n is an integer from 2 to 5 (SEQ ID NO: 1). See, Chen, X. et al. "Fusion protein linkers: property, design and functionality," *Adv. Drug Deliv. Rev.* (2013) 65 (10): 1357-69, which is entirely incorporated by reference. These linkers, which comprise (EAAAK) segments (SEQ ID NO: 2), can display alpha-helical conformation, which was stabilized by Glu-Lys salt bridges formed within each segment. In some cases, an alpha helix forming linker can comprise proline-rich sequence, such as, for example $(XP)_n$, wherein X is any amino acid and, in some cases, X is Ala, Lys, or Glu, and wherein n is an integer from 2 to 10 (SEQ ID NO: 9). In some cases, spacer peptide 204 can comprise $(EAAAK)_n$, wherein n is an integer from 2 to 5 (SEQ ID NO: 1). In some cases, spacer peptide 204 can comprise two or more fragments of $(EAAAK)_n$, wherein n is an integer from 2 to 5 (SEQ ID NO: 1). In some cases, spacer peptide 204 can comprise (Ala-Pro) 7 (SEQ ID NO: 3), $(Glu-Pro)_7$ (SEQ ID NO: 4), or $(Lys-Pro)_7$ (SEQ ID NO: 5). In some cases, spacer peptide 204 can comprise two or more members selected from the group consisting of (Ala-Pro), (Glu-Pro), and (Lys-Pro), wherein the two or more members are in tandem. In some examples, an alpha helical linker, such as, for example, LEA (EAAAK)$_4$ALE (SEQ ID NO: 6), LEA (EAAAK)$_4$ALEA (EAAAK)$_4$ALE (SEQ ID NO: 7), or LEA (EAAAK)$_4$ALEA (EAAAK)$_4$ALEA (EAAAK)$_4$ALE (SEQ ID NO: 8), can be prepared and inserted into a recombinant plasmid comprising DNAs of dCas9 protein 202 and endonuclease 206 according to the procedures described in Bai, Y. et al. "Improving the oral efficacy of recombinant granulocyte colony-stimulating factor and transferrin fusion protein by spacer optimization," *Pharm. Res.* (2006) 23 (9): 216-21, which is entirely incorporated herein by reference. In some cases, spacer peptide 204 can comprise more than one alpha-helical segments, wherein there are non-alpha-helical peptides inserted between alpha-helical segments.

Endonuclease 206, as used herein, generally refers to an enzyme capable of cleaving the phosphodiester bonds between the nucleotide subunits of nucleic acids within a polynucleotide chain. In some cases, the endonuclease 206 can comprise nonspecific (without preference to DNA sequence) endonuclease, such as, for example, DNase I, *Aspergillus* nuclease S(1), *Serratia marcescens* nuclease, staphylococcal nuclease, micrococcal nuclease, and DNase A. In some cases, the endonuclease 206 can comprise restriction endonuclease. In some cases, the endonuclease 206 can comprise nickase. The cleaved DNA products can have a blunt end, an overhang, or a sticky end.

Single guide RNA (sgRNA) 208 can be an RNA molecule that is a guide to localize the dCas9-RNA complex to a target nucleic acid sequence via base-pairing. The sgRNA 208 can comprise two domains: (1) a guide domain 210 that binds to a target nucleic acid (and directs binding of a dCas9/sgRNA complex to the same target nucleic acid); and (2) a domain that binds the dCas9 protein. Generally, the guide domain 210 of sgRNA 208 can comprise a sequence complementary to the target nucleic acid. As a result, dCas9 when complexed with sgRNA can target a specific nucleic acid sequence if dCas9 is co-expressed with an appropriate sgRNA. In some cases, sgRNA can comprise any polynucleotide sequence which has complementarity with a target nucleic acid to hybridize with and can direct sequence-specific binding of a nucleic acid-targeting complex to the target nucleic acid sequence. In some cases, the degree of complementarity, when aligned using a suitable alignment algorithm, can be about or more than about 50%, 60%, 75%, 80%, 85%, 90%, 95%, 97.5%, or 99%. In some cases, the 5' end of the sgRNA, e.g., the guide domain 210, can comprise from about 17 to about 24 nucleotides that are complementary to the target DNA. In some cases, the guide domain 210 of the sgRNA can comprise about 17-24, about 18-22, about 19-21, or about 20 nucleotides that are complementary to the target DNA. In some cases, the sgRNA can comprise a sequence complementary to adaptors attached to barcoded DNA fragments in a set of DNA fragments. In some cases, the sgRNA can comprise a sequence complementary to the P5 or P7 handle of an Illumina adaptor employed in NGS sequencing. In some cases, the sgRNA can comprise a sequence complementary to the sequence of an adaptor other than the P5 or P7 handle of the Illumina adaptor.

Turning back to FIG. 3, a mechanism of the CRISPR-Cas targeted endonuclease system 200 can be shown. The sgRNA 208 can specifically target a first barcoded fragment 220, which can comprise adapter arms 222 and 224, and strands 226 and 228 of a DNA insert. In the example shown in FIG. 3, the adapter arm 222 can be complementary to the guide domain 210 of sgRNA 208. Upon binding of the guide domain 210 to the adapter arm 222, the spacer peptide 204 can place the endonuclease 206 into the vicinity of the first barcoded fragment 220 downstream from the adaptor arm 222. Then the endonuclease 206 can make double strand breaks on strands 226 and 228 of the first barcoded fragment 220 at a site downstream of adaptor 222 to afford a second barcoded fragment 230. The second barcoded fragment 230 can comprise adaptor arms 222 and 224, and strands 232 and 234 of the DNA insert. Strands 232 and 234 can be shorter than strands 226 and 228. Further, strands 232 and 234 may have a blunt end, an overhang, or a sticky end, and may be further processed, e.g., to be ligated to another adaptor for NGS sequencing purposes.

In some cases, the size of the strands 232 and 234 can be predetermined and/or optimized by varying the structure of the spacer peptide 204 and/or the choice of endonuclease 206. In some cases, the size of the strands 232 and 234 can vary with the length of the spacer peptide 204 (i.e., a longer spacer peptide 204 leads to longer strands 232 and 234). In some cases, a plurality of the first barcoded fragments 220, which can comprise a plurality of the strands 226 and 228, can be processed by the CRISPR-Cas targeted endonuclease system 200 to produce a plurality of the second barcoded fragments 230 having a plurality of strands 232 and 234. In some cases, the plurality of strands 232 and 234 can be of the same length. In some cases, the plurality of strands 232 and 234 can be of different lengths. In some cases, the largest variation in lengths among the plurality of strands 232 and 234 can be about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, the plurality of strands 232 and 234 can have a tighter distribution in terms of insert sizes than the plurality of strands 226 and 228.

Process of Preparing DNA Samples with Length-Specified Insert Sizes

The present disclosure provides methods and systems for preparing set of DNA samples with length-specified insert sizes from sample nucleic acids. The improved process increases read quality of DNA sequencing and/or sequencing efficiency.

In some cases, a first set of barcoded fragments of sample nucleic acids can be made according to methods described herein. The members of the first set of barcoded fragments can be of varying lengths. In the presence of a CRISPR-Cas complex, e.g., a CRISPR-Cas targeted endonuclease system, a plurality of members in the first set of barcoded fragments can be processed to produce a second set of barcoded fragments comprising members of more uniformed lengths when compared with those in the first set of barcoded fragments.

Figure 4:
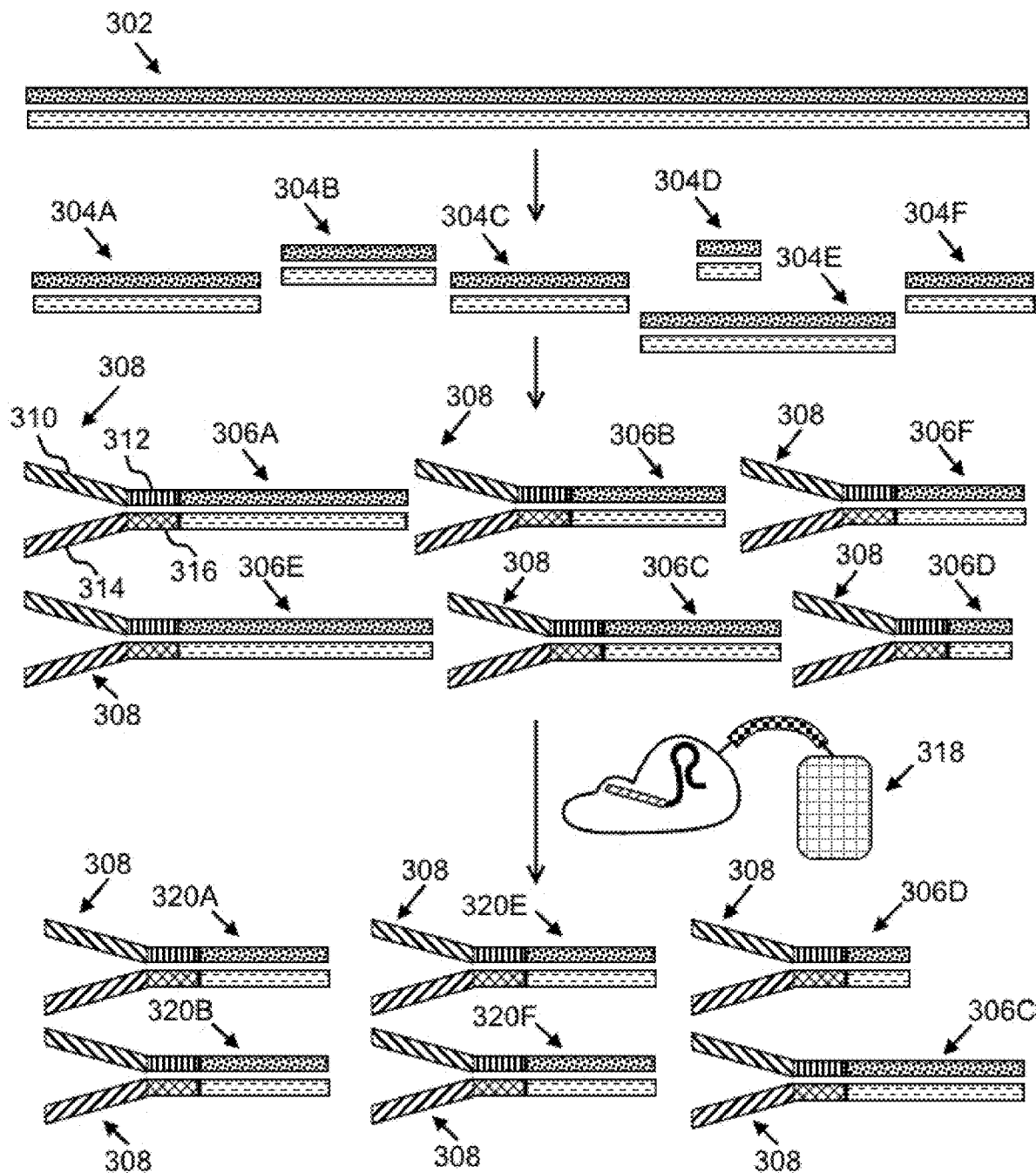
FIG. 4 is a diagram illustrating a process of converting a target nucleic acid into barcoded fragments with defined lengths using the CRISPR-Cas complex shown in FIG. 3.

One example process is illustrated in FIG. 4, which depicts the transformation of a sample nucleic acid 302 into a first set of barcoded fragments, which, in turn, can be converted further into a second set of barcoded fragments with length-specified insert sizes. As illustrated in FIG. 4, in the fragmenting operation, the sample nucleic acid 302 can be first fragmented and/or amplified to produce fragments 304A-304F with varying lengths. Each of fragments 304A-304F can comprise at least one end which can be processed and ligated to afford the first barcoded fragments 306A-306F by attaching a double stranded barcode oligonucleotide 308 to at least one end of each fragment. The double stranded barcode oligonucleotide 308 can comprise segments 310, 312, 314, and 316, wherein segments 312 and 316 are complementary to each other, and segments 310 and 314 are not complementary to each other, as shown. Hence, segments 310 and 314 can be single stranded, ready to hybridize with their respective complementary strands. In some cases, segment 310 can comprise a P5 segment. In some cases, segment 314 can comprise a P7 segment.

A CRISPR-Cas targeted endonuclease system 318, similar to what is described in FIG. 3, can target either segment 310 or segment 314 of the adaptor 308 via its sgRNA component due to sequence complementarity. For example, upon binding of the CRISPR-Cas targeted endonuclease system 318 to the first barcoded fragments 306A, the endonuclease of the CRISPR-Cas targeted endonuclease system 318 can make a double strand cut on the first barcoded fragment 306A by its tethered endonuclease to afford a new, shorter second barcoded fragment 320A. Similar transformations in the presence of the CRISPR-Cas targeted endonuclease system 318 can convert the first barcoded fragments 306B, 306E, and 306F into the second barcoded fragments 320B, 320E, and 320F, respectively. The first barcoded fragment 306C may remain unchanged due to unfavorable interaction with either the spacer peptide or the endonuclease of the CRISPR-Cas targeted endonuclease system 318. The first barcoded fragment 306D may also remain intact because it is too short for the endonuclease of the CRISPR-Cas targeted endonuclease system 318 to make the double strand cuts.

In some cases, the second barcoded fragments 320A, 320B, 320E, and 320F are of the same insert size. In some cases, the second barcoded fragments 320A, 320B, 320E, and 320F are of different insert sizes. In some cases, the second barcoded fragments 320A, 320B, 320E, and 320F can display a tighter distribution in terms of insert sizes when compared with their precursors, the first barcoded fragments 306A, 306B, 306E, and 306F. In some cases, the largest variation in insert sizes among the second barcoded fragments 320A, 320B, 320E, and 320F can be about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. As used herein, a tighter distribution in insert sizes generally refers to more insert sizes distributed toward the mean of all insert sizes. A tighter distribution may indicate that there is less variation among all insert sizes. For example, when distribution of insert sizes is drawn in a curve, a tighter distribution curve corresponds to a tighter bell-shape, i.e., with a smaller standard deviation.

Overall, in the presence of the CRISPR-Cas targeted endonuclease system 318, the first set of barcoded fragments comprising the first barcoded fragments 306A-306F can be transformed into the second set of barcoded fragments comprising the unchanged first barcoded fragments 306C-306D and the second barcoded fragments 320A, 320B, 320E, and 320F. As shown in FIG. 4, the second barcoded fragments 320A, 320B, 320E, and 320F can be of more uniformed lengths when compared with their precursors in the first barcoded set of fragments, i.e., the first barcoded fragments 306A, 306B, 306E, and 306F. Consequently, the CRISPR-Cas targeted endonuclease system 318 provides a tighter distribution of insert sizes among members of the second set of barcoded fragments.

Additional Barcoding

Figure 5A:
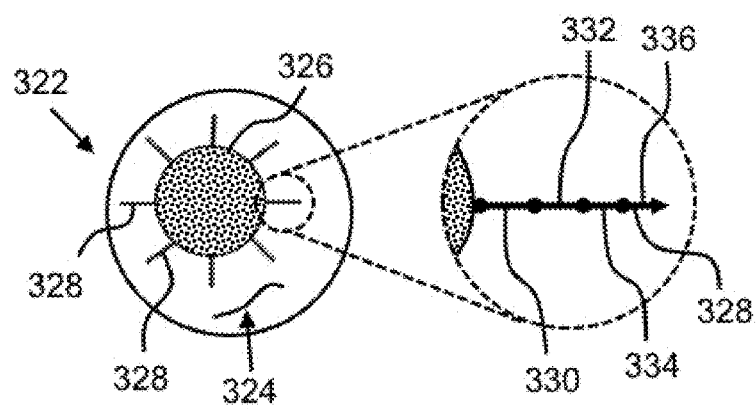
FIG. 5A schematically illustrates an overview of an example process for preparation of a set of barcoded sequencing samples.
Figure 5B:
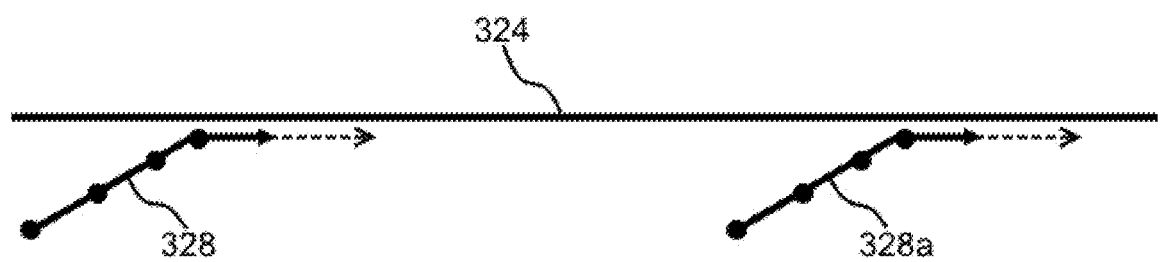
FIG. 5B schematically illustrates an operation in a process for preparation of a set of barcoded sequencing samples.
Figure 5C:
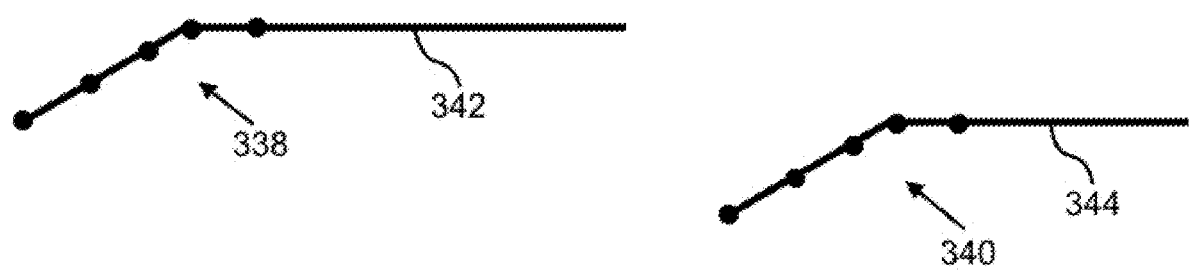
FIG. 5C schematically illustrates another operation in a process for preparation of a set of barcoded sequencing samples.

Additional barcoding methods are possible. In one embodiment, as shown in FIGS. 5A-5C and as described in U.S. patent application Ser. No. 14/316,383, filed Jun. 26, 2014, which is entirely incorporated herein by reference, an example process to prepare barcoded fragments of template nucleic acids as a set of sequencing samples is shown using droplets 322. As shown in FIG. 5A, a sample nucleic acid 324 may co-partition with a bead 326 in a droplet 322 in an emulsion. Within the droplet 322, oligonucleotides 328 may be provided on the bead 326. The oligonucleotides 328 may be released from the bead 326 and become reagents within the droplet 322. As shown in FIG. 5A, each oligonucleotide 328 may include a barcode sequence 332, in addition to one or more functional sequences, e.g., sequences 330, 334 and 336. For example, sequence 330 may function as an attachment or immobilization sequence for a given sequencing system, e.g., a P5 sequence used for attachment in flow cells of an Illumina Hiseq or Miseq system. Sequence 336 may be a primer such as, for example, a universal, random or targeted N-mer for priming replication of portions of the sample nucleic acid 324. Sequence 334 may provide a sequencing priming region, such as a "read1" or R1 priming region that is used to prime polymerase mediated, template directed sequencing by synthesis reactions in sequencing systems. In many cases, the barcode sequence 332, immobilization sequence 330 and R1 sequence 334 may be common to all of the oligonucleotides 328 attached to a given bead. The primer sequence 336 may vary for random N-mer primers, or may be common to the oligonucleotides 328 on a given bead for certain targeted applications. Although described with reference to the specific positioning and type of functional sequence segment elements within the barcode oligonucleotides 328, the position and nature of the functional segments within a barcode oligonucleotide 328 may vary. For example, primer sequences for different sequencing systems may be employed in place of the P5 or read1 primers. Additionally, in some cases, the positional context of the different segments may be changed. For example, in some cases, the barcode sequence segment may be placed at the 5' end of the sequence read primer or R1 segment 334, e.g., between segments 334 and 336, so that the barcode can be sequenced in a first pass or initial sequence read, e.g., following priming of the read1 sequence during the sequencing of the resultant barcoded fragments, as opposed to obtaining the barcode read on a subsequent sequencing read of a reverse complement.

Based upon the presence of primer sequence 336, the oligonucleotides 328 and 328a may be able to prime the sample nucleic acid 324 as shown in FIG. 5B, which may allow for extension of the oligonucleotides 328 and 328a annealed on the sample nucleic acid 324 in the presence of polymerase enzymes and other extension reagents, which may also be co-partitioned with the bead 326 and sample nucleic acid 324. The polymerase enzymes may include thermostable polymerases, e.g., where initial denaturation of double stranded sample nucleic acids within the partitions is desired. Alternatively, denaturation of sample nucleic acids may precede partitioning, such that single stranded target nucleic acids may be deposited into the partitions, allowing the use of non-thermostable polymerase enzymes, e.g., Klenow, phi29 DNA polymerase, DNA polymerase lambda (Pol1), and the like. As shown in FIG. 5B, extension of the oligonucleotides 328 and 328a may anneal to multiple different regions of the sample nucleic acid 324. Consequently, multiple overlapping complements or fragments of the sample nucleic acid 324 can be created, e.g., fragments 338 and 340 as shown in FIG. 5C. Although fragments 338 and 340 may comprise sequences that are complementary to sample nucleic acid 324, e.g., insert sequences 342 and 344 (also referred to as "inserts"), these fragments herein may generally be referred to as comprising fragments of the sample nucleic acid 324, having the attached barcode sequences. These insert sequences 342 and 344 may then be subjected to sequence analysis, or they may be subjected to further processing.

Figure 6A:
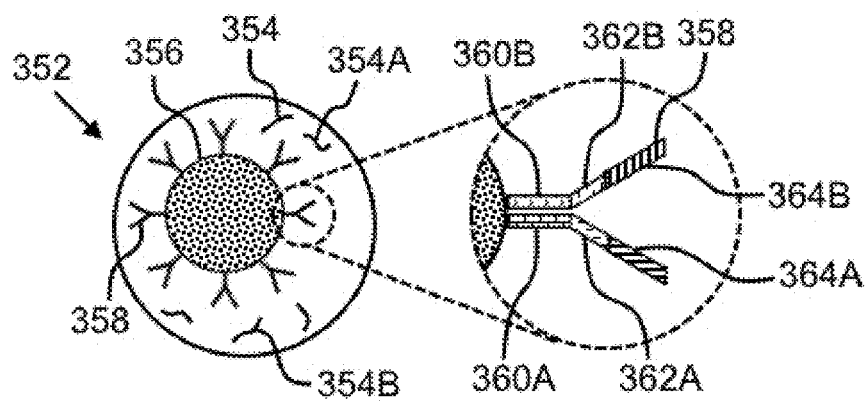
FIG. 6A schematically illustrates an overview of an example process for preparation of a set of Y-adapter barcoded sequencing samples.
Figure 6B:
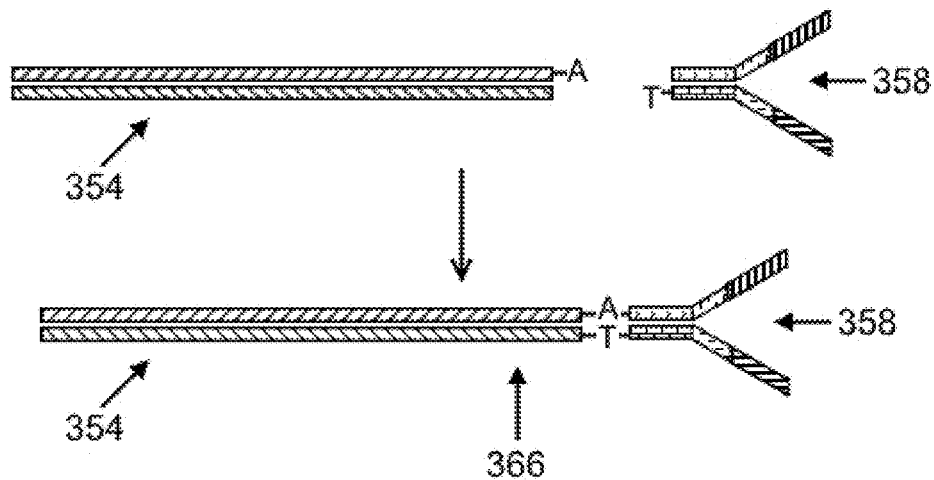
FIG. 6B schematically illustrates an operation in a process for preparation of a set of Y-adapter barcoded sequencing samples.
Figure 6C:
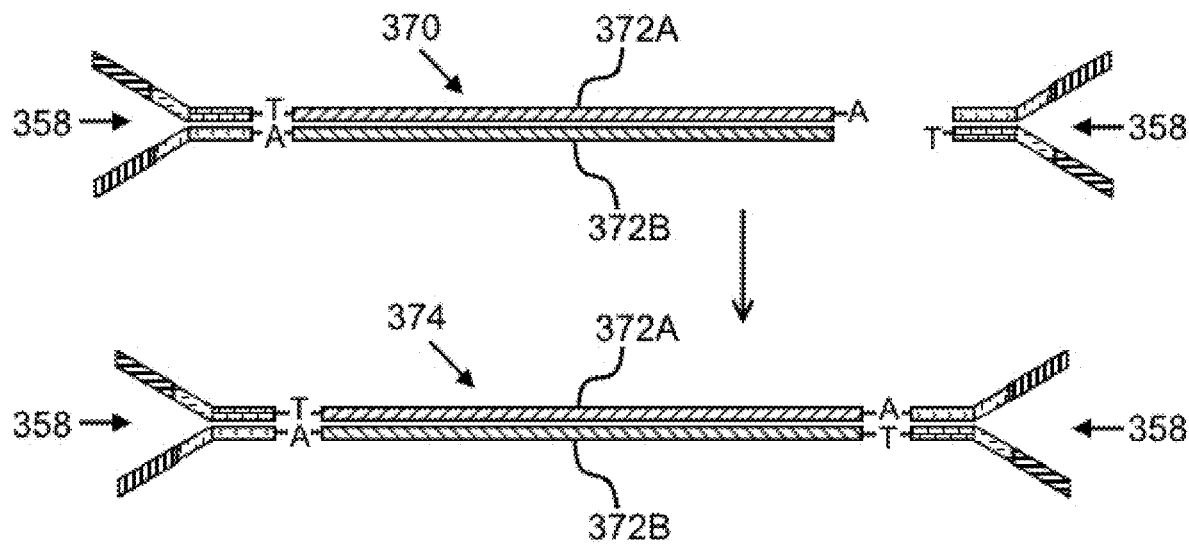
FIG. 6C schematically illustrates another operation in a process for preparation of a set of Y-adapter barcoded sequencing samples.

Another embodiment is illustrated in FIGS. 6A-6C, which sets forth an example process of making a set of sequencing samples with Y-adapters to afford barcoded fragments of template nucleic acids in droplets 352. As shown in FIG. 6A, fragments 354, 354A, 354B, etc., can co-partition with a bead 356 in a droplet 352 in an emulsion. Within the droplet 352, Y-adapters 358 may be provided on the bead 356. A Y-adapter 358 can comprise Read1primer segment 360A, Read2primer segment 360B, barcode segments 362A and 362B, functional segments 364A and 364B. Functional segment 364A can be P5 sequence while functional segment 364B can be P7 sequence. In addition, there may be a non-paired deoxythymidine nucleotide overhang (shown as "T") at the 3'-end of the double-stranded end. Alternatively, the T-base overhand can be added at the 3'-end of the Y-adapter 358 after the Y-adapter 358 is released from the bead. In addition, the Y-adapters 358, with or without the T-base overhang, may be released from the bead 356 and may become reagents within the droplet 352 thereafter. Although functional segments 364A and 364B are shown as P5/P7 sequences, which can be used for attachment in flow cells of an Illumina Hiseq or Miseq system, other type of sequences can be included in functional segments 364A and 364B as well. In many cases, the Read1primer segment 360A, the Read2primer segment 360B, the barcode segments 362A and 362B, and functional segments 364A and 364B may be common to all of the Y-adapters 358 attached to a given bead. Alternatively, the barcode segments may vary on different beads. Although described with reference to the specific positioning and type of functional sequence segment elements within a Y-adapter 358, the position and nature of the functional segments within a Y-adapter 358 may vary.

Once released from the bead and with required T-base overhang, the Y-adapters 358 can be ligated to DNA fragments, such as, for example, DNA fragment 354, as shown in FIG. 6B. A standard ligation enzyme system, e.g., a T4 ligase, can be used to ligate an A-tailed DNA fragment 354 with the Y-adaptor comprising a T-base overhang. As a result, a barcoded, double stranded fragment 366 can be obtained. The barcoded fragment 366 can then be subjected to one or more additional processing operations, e.g., to be cut by a CRISPR-Cas complex, e.g. a CRISPR-Cas targeted endonuclease system, or be ligated with another Y-adapter at the other end of the DNA fragment, if desired.

In another embodiment, once released from the bead, the Y-adapters 358 can be ligated to DNA fragments, such as, for example, DNA fragment 370, as shown in FIG. 6C. DNA fragment 370 can comprise complementary DNA strands 372A and 372B, and a ligated Y-adapter on one end of the DNA strands 372A and 372B. In addition, the 3'-end of DNA strand 372A can be A-tailed, either while in droplet 352 or before entering droplet 352. Such treatment of DNA fragment 370 can be accomplished by a combination of fill-in reactions and exonuclease activity to make blunt-end DNA fragments, followed by A-tailing. For example, to accomplish end-repair reactions, T4 DNA polymerase can digest 3' protruding ends; Klenow DNA polymerase can extend 3' recessive ends; and T4 polynucleotide kinase can phosphorylate 5'-ends or dephosphorylate 3'-ends, including those of protruding and blunt ends. A-tailing at 3'-end can be accomplished by using Taq DNA Polymerase and deoxyadenosine triphosphate (dATP). Then a standard ligation enzyme system, e.g., a T4 ligase, can be used to ligate the A-tailed DNA fragment 370 with the Y-adaptor 358 with a T-base overhang. As a result, a paired-end, barcoded, double stranded fragment 374 can be obtained. The paired-end, barcoded fragment 374 can then be subjected to one or more additional processing operations, e.g., to be amplified, or to be sequenced.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

Figure 8:
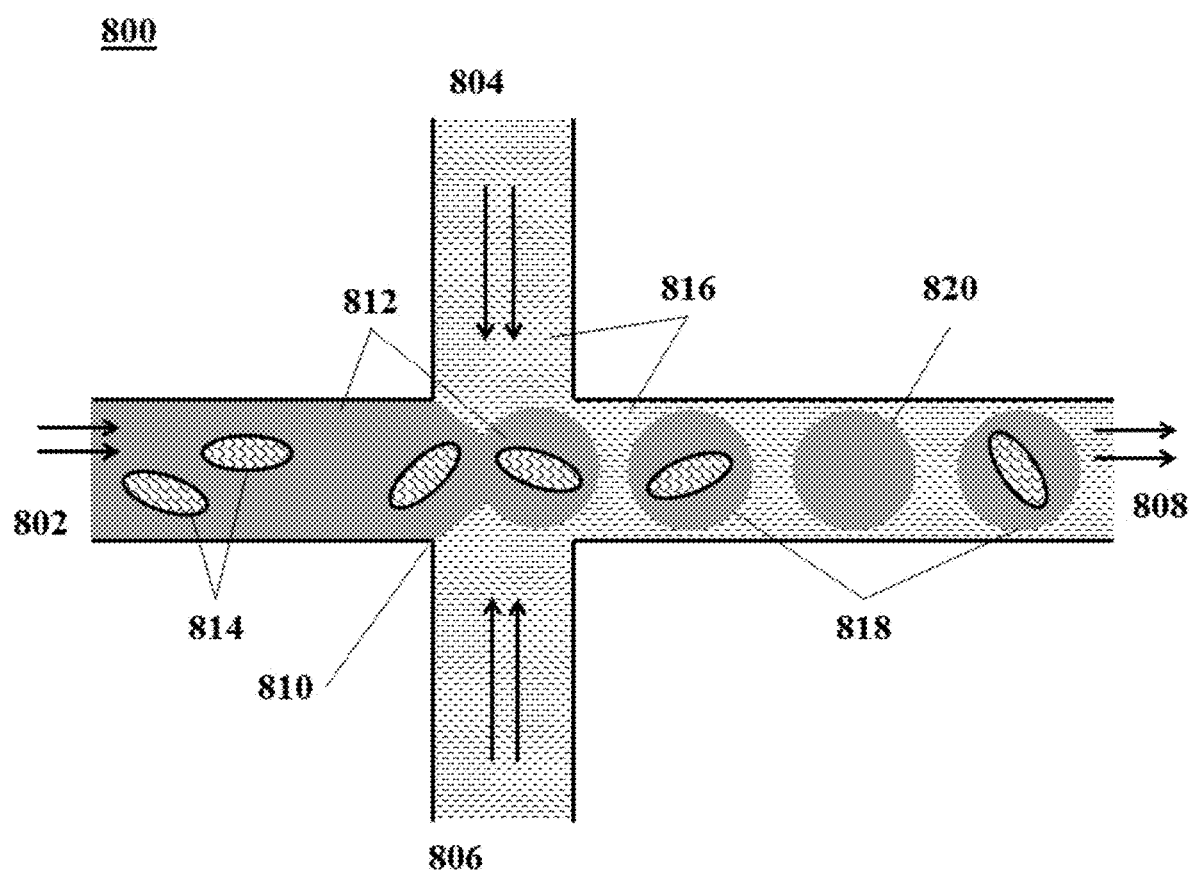
FIG. 8 shows an example of a microfluidic channel structure for partitioning individual biological particles.

FIG. 8 shows an example of a microfluidic channel structure 800 for partitioning individual biological particles. The channel structure 800 can include channel segments 802, 804, 806 and 808 communicating at a channel junction 810. In operation, a first aqueous fluid 812 that includes suspended biological particles (or cells) 814 may be transported along channel segment 802 into junction 810, while a second fluid 816 that is immiscible with the aqueous fluid 812 is delivered to the junction 810 from each of channel segments 804 and 806 to create discrete droplets 818, 820 of the first aqueous fluid 812 flowing into channel segment 808, and flowing away from junction 810. The channel segment 808 may be fluidically coupled to an outlet reservoir where the discrete droplets can be stored and/or harvested. A discrete droplet generated may include an individual biological particle 814 (such as droplets 818). A discrete droplet generated may include more than one individual biological particle 814 (not shown in FIG. 8). A discrete droplet may contain no biological particle 814 (such as droplet 820). Each discrete partition may maintain separation of its own contents (e.g., individual biological particle 814) from the contents of other partitions.

The second fluid 816 can comprise an oil, such as a fluorinated oil, that includes a fluorosurfactant for stabilizing the resulting droplets, for example, inhibiting subsequent coalescence of the resulting droplets 818, 820. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 800 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 818, containing one or more biological particles 814, and (2) unoccupied droplets 820, not containing any biological particles 814. Occupied droplets 818 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 814) at the partitioning junction 810, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 802), or other fluids directed into the partitioning junction (e.g., in channel segments 804, 806) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 8, may be readily used in encapsulating cells as described herein. In particular, and with reference to FIG. 8, the aqueous fluid 812 comprising (i) the biological particles 814 and (ii) the polymer precursor material (not shown) is flowed into channel junction 810, where it is partitioned into droplets 818, 820 through the flow of non-aqueous fluid 816. In the case of encapsulation methods, non-aqueous fluid 816 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 816 in channel segments 804 and 806, which can initiate the copolymerization of the acrylamide and BAC into a cross-linked polymer network, or hydrogel.

Upon contact of the second fluid stream 816 with the first fluid stream 812 at junction 810, during formation of droplets, the TEMED may diffuse from the second fluid 816 into the aqueous fluid 812 comprising the linear polyacrylamide, which will activate the crosslinking of the polyacrylamide within the droplets 818, 820, resulting in the formation of gel (e.g., hydrogel) microcapsules, as solid or semi-solid beads or particles entraining the cells 814. Although described in terms of polyacrylamide encapsulation, other 'activatable' encapsulation compositions may also be employed in the context of the methods and compositions described herein. For example, formation of alginate droplets followed by exposure to divalent metal ions (e.g., Ca' ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

Figure 9:
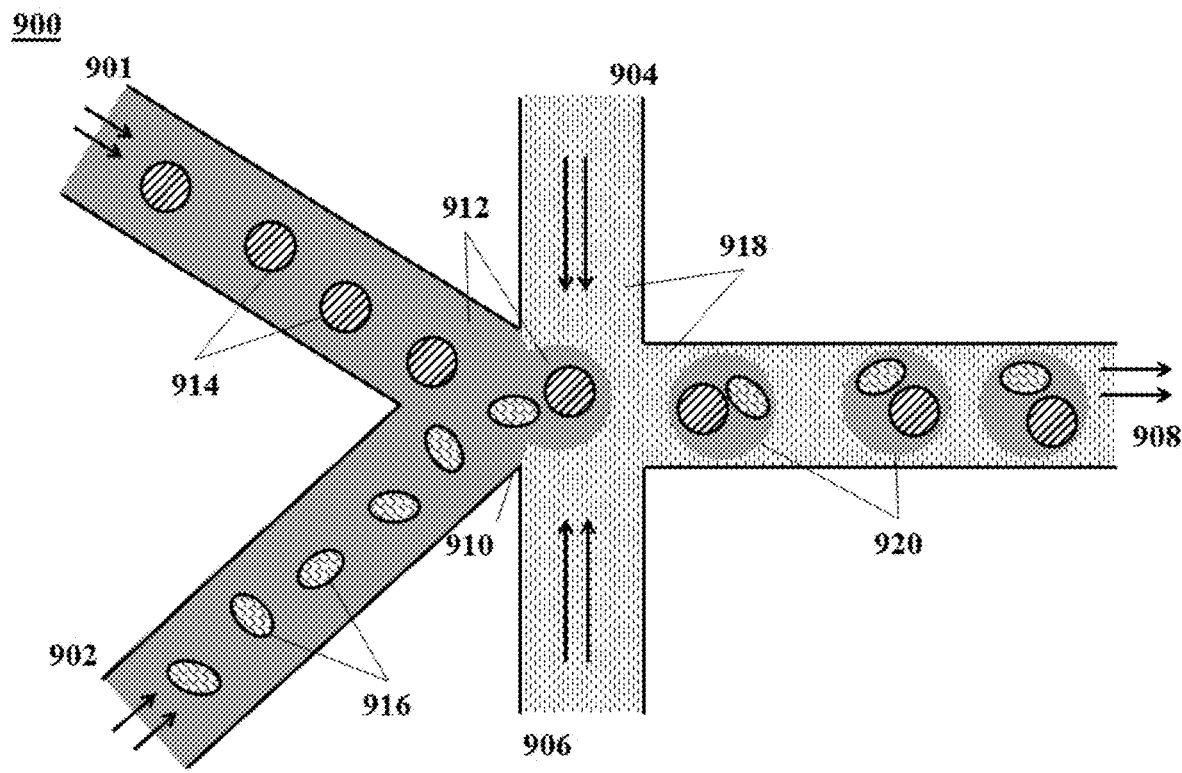
FIG. 9 shows an example of a microfluidic channel structure for delivering barcode carrying beads to droplets.

FIG. 9 shows an example of a microfluidic channel structure 900 for delivering barcode carrying beads to droplets. The channel structure 900 can include channel segments 901, 902, 904, 906 and 908 communicating at a channel junction 910. In operation, the channel segment 901 may transport an aqueous fluid 912 that includes a plurality of beads 914 (e.g., with nucleic acid molecules, oligonucleotides, molecular tags) along the channel segment 901 into junction 910. The plurality of beads 914 may be sourced from a suspension of beads. For example, the channel segment 901 may be connected to a reservoir comprising an aqueous suspension of beads 914. The channel segment 902 may transport the aqueous fluid 912 that includes a plurality of biological particles 916 along the channel segment 902 into junction 910. The plurality of biological particles 916 may be sourced from a suspension of biological particles. For example, the channel segment 902 may be connected to a reservoir comprising an aqueous suspension of biological particles 916. In some instances, the aqueous fluid 912 in either the first channel segment 901 or the second channel segment 902, or in both segments, can include one or more reagents, as further described below. A second fluid 918 that is immiscible with the aqueous fluid 912 (e.g., oil) can be delivered to the junction 910 from each of channel segments 904 and 906. Upon meeting of the aqueous fluid 912 from each of channel segments 901 and 902 and the second fluid 918 from each of channel segments 904 and 906 at the channel junction 910, the aqueous fluid 912 can be partitioned as discrete droplets 920 in the second fluid 918 and flow away from the junction 910 along channel segment 908. The channel segment 908 may deliver the discrete droplets to an outlet reservoir fluidly coupled to the channel segment 908, where they may be harvested.

As an alternative, the channel segments 901 and 902 may meet at another junction upstream of the junction 910. At such junction, beads and biological particles may form a mixture that is directed along another channel to the junction 910 to yield droplets 920. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 918 can comprise an oil, such as a fluorinated oil, that includes a fluorosurfactant for stabilizing the resulting droplets, for example, inhibiting subsequent coalescence of the resulting droplets 920.

A discrete droplet that is generated may include an individual biological particle 916. A discrete droplet that is generated may include a barcode or other reagent carrying bead 914. A discrete droplet generated may include both an individual biological particle and a barcode carrying bead, such as droplets 920. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 900 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 910), such as through an additional channel or channels upstream of the channel junction. In accordance with other aspects, additionally or alternatively, biological particles may be partitioned along with other reagents, as will be described further below.

Figure 10:
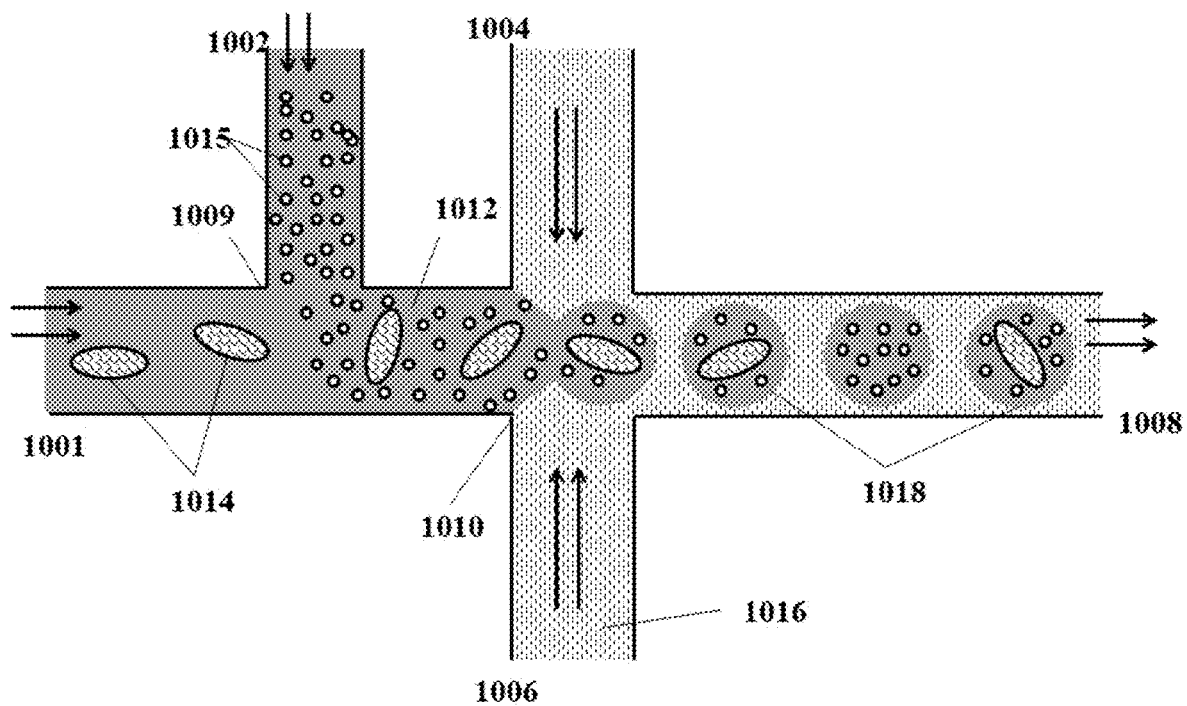
FIG. 10 shows an example of a microfluidic channel structure for co-partitioning biological particles and reagents.

FIG. 10 shows an example of a microfluidic channel structure 1000 for co-partitioning biological particles and reagents. The channel structure 1000 can include channel segments 1001, 1002, 1004, 1006 and 1008. Channel segments 1001 and 1002 communicate at a first channel junction 1009. Channel segments 1002, 1004, 1006, and 1008 communicate at a second channel junction 1010.

In an example operation, the channel segment 1001 may transport an aqueous fluid 1012 that includes a plurality of biological particles 1014 along the channel segment 1001 into the second junction 1010. As an alternative or in addition to, channel segment 1001 may transport beads (e.g., gel beads). The beads may comprise barcode molecules.

For example, the channel segment 1001 may be connected to a reservoir comprising an aqueous suspension of biological particles 1014. Upstream of, and immediately prior to reaching, the second junction 1010, the channel segment 1001 may meet the channel segment 1002 at the first junction 1009. The channel segment 1002 may transport a plurality of reagents 1015 (e.g., lysis agents) suspended in the aqueous fluid 1012 along the channel segment 1002 into the first junction 1009. For example, the channel segment 1002 may be connected to a reservoir comprising the reagents 1015. After the first junction 1009, the aqueous fluid 1012 in the channel segment 1001 can carry both the biological particles 1014 and the reagents 1015 towards the second junction 1010. In some instances, the aqueous fluid 1012 in the channel segment 1001 can include one or more reagents, which can be the same or different reagents as the reagents 1015. A second fluid 1016 that is immiscible with the aqueous fluid 1012 (e.g., oil) can be delivered to the second junction 1010 from each of channel segments 1004 and 1006. Upon meeting of the aqueous fluid 1012 from the channel segment 1001 and the second fluid 1016 from each of channel segments 1004 and 1006 at the second channel junction 1010, the aqueous fluid 1012 can be partitioned as discrete droplets 1018 in the second fluid 1016 and flow away from the second junction 1010 along channel segment 1008. The channel segment 1008 may deliver the discrete droplets 1018 to an outlet reservoir fluidly coupled to the channel segment 1008, where they may be harvested.

The second fluid 1016 can comprise an oil, such as a fluorinated oil, that includes a fluorosurfactant for stabilizing the resulting droplets, for example, inhibiting subsequent coalescence of the resulting droplets 1018.

A discrete droplet generated may include an individual biological particle 1014 and/or one or more reagents 1015. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 1000 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

Computer Control System

Figure 7:
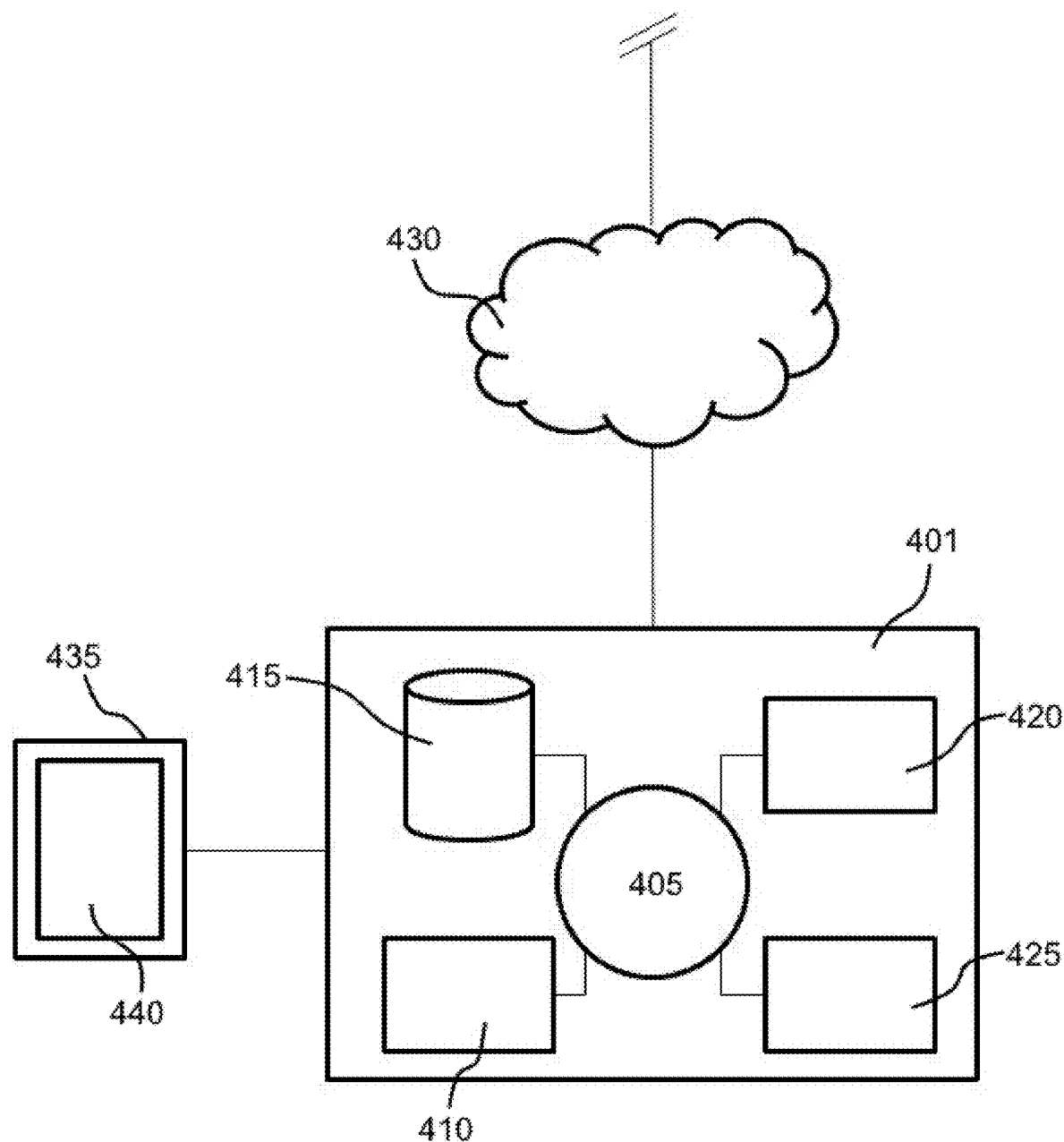
FIG. 7 shows an example computer control system that is programmed or otherwise configured to implement methods provided herein.

The present disclosure provides computer control systems that are programmed to implement methods of the disclosure. FIG. 7 shows a computer system 401 that is programmed or otherwise configured to implement methods of the disclosure including fragmentation of nucleic acid samples, construction of sets of fragments, nucleic acid sequencing methods, and interpretation of nucleic acid sequencing data. The computer system 401 can be an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., APPLE® iPad, SAMSUNG® Galaxy Tab), telephones, Smart phones (e.g., APPLE® iPhone, Android-enabled device, BLACKBERRY®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" generally refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. Shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, results of nucleic acid sequencing, analysis of nucleic acid sequencing data, characterization of nucleic acid sequencing samples, cell characterizations, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, monitor and change reaction conditions, initiate nucleic acid sequencing, process nucleic acid sequencing data, interpret nucleic acid sequencing results, characterize nucleic acid samples, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those

What is claimed is:

1. A method for preparing a set of nucleic acid molecules, comprising:
   (a) providing a plurality of partitions comprising (i) a plurality of adapters, each comprising an adapter sequence, and (ii) a plurality of deoxyribonucleic acid (DNA) fragments, wherein said plurality of adapters comprise barcode molecules comprising a plurality of different barcode sequences, and wherein barcode molecules within a partition comprise a common barcode sequence;
   (b) within said plurality of partitions, ligating said plurality of adapters and said plurality of DNA fragments to synthesize a plurality of barcoded nucleic acid molecules, wherein each barcoded nucleic acid molecule of said plurality of barcoded nucleic acid molecules comprises (i) said adapter sequence and (ii) a barcode sequence of said plurality of different barcode sequences or a complement thereof;
   (c) providing a Clustered Regularly Interspaced Palindromic Repeats (CRISPR)-CRISPR associated protein (Cas) (CRISPR-Cas) complex that comprises (i) a fusion protein comprising (I) a first protein, (II) a second protein that is a site-specific endonuclease, and (III) a polypeptide linking said first protein and said second protein, wherein said polypeptide comprises a length between 150 and 700 amino acids, and (ii) a guide ribonucleic acid (RNA) capable of binding to said first protein and selectively coupling to said adapter sequence, wherein said first comprises protein is a type II or type V CRISPR-Cas RNA-guided DNA endonuclease that lacks endonuclease activity, wherein said guide RNA comprises a sequence complementary to said adapter sequence; and
   (d) bringing said plurality of barcoded nucleic acid molecules in contact with said CRISPR-Cas complex under conditions sufficient for (i) said guide RNA to couple to said adapter sequence of said plurality of barcoded nucleic acid molecules and (ii) said second protein to cleave said plurality of barcoded nucleic acid molecules, thereby providing said set of nucleic acid molecules, wherein nucleic acid molecules of said set of nucleic acid molecules each (I) a barcode sequence of said plurality of different barcode sequences, or a complement thereof, and (II) a shortened DNA fragment of said plurality of DNA fragments.

2. The method of claim 1, wherein said polypeptide comprises an alpha-helix-forming linker.

3. The method of claim 1, wherein said plurality of DNA fragments comprises DNA fragments of varying lengths.

4. The method of claim 1, wherein said second protein comprises a restriction endonuclease.

5. The method of claim 1, wherein said adapter sequence comprises P5 adapter or P7 adapter.

6. The method of claim 1, wherein said plurality of partitions are wells, microwells, tubes, vials, microcapsules, or droplets within an emulsion.

7. The method of claim 1, wherein said plurality of partitions are aqueous droplets within a water-in-oil emulsion.

8. The method of claim 1, wherein said guide RNA comprises a chimeric RNA that comprises a guide sequence and a tracr sequence.

9. The method of claim 1, wherein said guide RNA comprises a sequence of 17 nucleotides to 24 nucleotides complementary to said adapter sequence.

10. The method of claim 1, wherein said guide RNA comprises a hairpin sequence of 35 nucleotides to 50 nucleotides, wherein said hairpin binds said first protein.

11. The method of claim 1, wherein said set of nucleic acid molecules in (d) display a tighter distribution in terms of lengths when compared with said plurality of barcoded nucleic acid molecules.

12. The method of claim 11, wherein a largest variation in lengths among said nucleic acid molecules in said set of nucleic acid molecules in (d) is from 1 to 500 nucleotides.

13. The method of claim 1, wherein, in (a), said plurality of adapters are coupled to a plurality of beads in said plurality of partitions.

14. The method of claim 13, wherein said ligating in (b) comprises releasing said plurality of adapters from said plurality of beads within said plurality of partitions.

15. The method of claim 1, wherein said polypeptide comprises an unstructured peptide.

16. The method of claim 1, wherein said polypeptide comprises a positively charged group.

17. The method of claim 16, wherein the positively charged group couples to a portion of a nucleic acid molecule of said nucleic acid molecules.

18. The method of claim 1, wherein said polypeptide comprises a proline.

19. The method of claim 1, further comprising amplifying said nucleic acid molecules of said set of nucleic acid molecules.

20. The method of claim 1, further comprising sequencing said nucleic acid molecules of said set of nucleic acid molecules.

* * * * *